(12) United States Patent
LaRue et al.

(10) Patent No.: US 11,179,085 B2
(45) Date of Patent: Nov. 23, 2021

(54) ANALYZING EEG WITH SINGLE-PERIOD SINGLE-FREQUENCY SINUSOIDS

(71) Applicants: James Patrick LaRue, Hanahan, SC (US); Denise Suarez LaRue, Hanahan, SC (US)

(72) Inventors: James Patrick LaRue, Hanahan, SC (US); Denise Suarez LaRue, Hanahan, SC (US)

( * ) Notice: Subject to any disclaimer, the term of this patent is extended or adjusted under 35 U.S.C. 154(b) by 176 days.

(21) Appl. No.: 16/510,842

(22) Filed: Jul. 12, 2019

(65) Prior Publication Data

US 2021/0007622 A1 Jan. 14, 2021

(51) Int. Cl.
*A61B 5/372* (2021.01)
*A61B 5/00* (2006.01)
*A61B 5/291* (2021.01)
*A61B 5/316* (2021.01)
*A61B 5/374* (2021.01)

(52) U.S. Cl.
CPC .............. *A61B 5/291* (2021.01); *A61B 5/316* (2021.01); *A61B 5/374* (2021.01); *A61B 5/4082* (2013.01); *A61B 5/6814* (2013.01); *A61B 5/4094* (2013.01); *A61B 5/7203* (2013.01); *A61B 5/7257* (2013.01); *A61B 5/742* (2013.01)

(58) Field of Classification Search
None
See application file for complete search history.

*Primary Examiner* — Etsub D Berhanu

(57) ABSTRACT

A technical solution is described for implementing a computer-executed signal processing algorithm to search for time domain segments of a recorded electroencephalogram (EEG) that are highly correlated, either positively or negatively, to one or more, individual, synthetically generated, single-period single-frequency (SPSF) sinusoids. The SPSFs are motivated by the combined concepts of individual Striatal Beat Frequencies (SBF) used to model cortical neuron activity, Frequency Domain Reflectometry used to study Voltage Standing Wave Ratios (VSWR), Geophysics Seismograms, and ghosting effects of multipath passing through periodic sinusoids. This computationally intense approach is only recently realizable through the advent of high performance computing. The SPSF approach, since it is not constrained to the error-laden one-window-fits-all approach of the Time-Frequency Spectrogram, offer's a more detailed basis to assess, and truer visualization of, the health of brain's electrical activities. This approach is a push-back against the Uncertainty Principal.

3 Claims, 16 Drawing Sheets

Zoom-in with box for table

Center point sample number where SPSF window applied

ANALYZING EEG WITH SINGLE-PERIOD SINGLE-FREQUENCY SINUSOIDS

CROSS-REFERENCE TO RELATED APPLICATIONS

N/A

STATEMENT REGARDING FEDERALLY SPONSORED RESEARCH OR DEVELOPMENT

N/A

REFERENCE TO SEQUENCE LISTING, A TABLE, OR A COMPUTER PROGRAM LISTING COMPACT DISC APPENDIX

N/A

BACKGROUND OF THE INVENTION

The present invention is primarily directed to the time-domain analysis of an electroencephalogram (EEG) as it pertains to determining the health of a brain's electrical activity and in particular to the analysis of brain activity for patients with Parkinson's or Alzheimer's disease. The present method may be viewed as a complement to magnetic resonance imaging (MRI). The method may also apply to the fields of Seismology from Geophysics and other time domain systems of vibration involving sound and light.

This invention is motivated, in part, by the concept of Striatal Beat Frequency (SBF); the assumption that cortical neurons fire in an oscillatory manner. The invention is also motivated, in part, by the belief that traditional Time-Frequency Discrete Fourier Transform (TF DFT) spectral analysis techniques, used to estimate the brain's electrical response, do not allow for the level of detail to isolate the conceptual SBFs.

For patients who require an analysis of the electrical activity of their brain, a typical non-invasive approach is to record an electroencephalogram (EEG) in order to perform a time-domain analysis of the signal. Historically, the time-domain analysis has been visualized as a time-frequency (TF) spectrogram which is a collection of Discrete Fourier Transforms (DFT) concatenated in columnar form. In this use case the EEG is partitioned into a set of overlapping windows; both the window size and the amount of overlap are predetermined and do not change. A DFT is calculated on each window and it is said DFTs that are concatenated in columnar form to produce a TF spectrogram. However, the use of windowing in this way leads to sources of error, some of which are rooted in the periodicity of the frequency components and the (sometimes overly ambitious) expectation of what a (Discrete and finite) Fourier Transform (DFT) provides in the way of identifying specific spectral components; three such sources are described next.

A first source of error comes from the fact the DFT is most accurate in identifying a specific spectral component when the sinusoidal waveform for each frequency component is continuous in the window, i.e., there is no on/off switching allowed; with the switching of states, there is error.

A second source of error comes from the DFT's expectation the individual frequency waveform is perfectly periodic, meaning the (discretely) sampled endpoint is (one point shy of) an integral multiple of the period for that single frequency component; with any window of samples containing less or more than said integral multiple, there is error.

A third source of error comes from the DFT's expectation that the individual frequency waveform maintains constant amplitude across a prolonged window of EEG. If there is a change of amplitude in any way, there is error.

Thus, while a particular size of window may satisfy the conditions for meeting the DFT's expectation for (discrete) continuity and exact periodicity for a few frequency components, from a practical standpoint, these conditions cannot be met for all spectral components; there has been an accepted tradeoff in accuracy vs the inevitable smearing of spectral characterization. In short, the TF approaches that are used to estimate true spectral content are limited by the 'one window fits all' approach which inevitably introduces error.

In general, TF plots have the appearance of smearing in the horizontal direction. This is due to the effects of the sliding window. There has been much work done in the area of choosing windows types to compact this artifact. These unwanted artifacts are usually attributed to the uncertainty principle as it applies to much of the signal processing domain. Other methods have been tried, such as wavelets, empirical mode decomposition, and the damped-oscillator oscillator detector method. Many of the end results show improvement in TF resolution however, these methods are still self-restricted to a single window size and these methods involve convolution and Fourier transforms which, due to the change in the periodicity of a single spectral component within a window, inevitable leads to spreading of the signal or the introduction of invalid spectral components.

FIGS. 2 through 4 act as visual examples to where the sources of error may come from and how these errors may be manifested in TF Spectrograms. FIG. 2 is an example to show the limitations to making accurate appraisals of spectral content from both properly and improperly windowed waveforms. The example uses a 10 Hz frequency component that is sampled 1000 samples per second so that one period of this waveform consists of 100 points. In FIG. 2, plots A-E show different applications of a 10 Hz sinusoid. Plots (F-J) are corresponding DFT of plots (A-E).

Pointer (21) indicates the end of a single period of a discretely sampled 10 Hz sinusoid. In plot F the spectral resolution is 10 Hz per mark and pointer (22) indicates the presence of a 10 Hz. Pointed (23) has been placed there is show that there is no 20 Hz component; the same observation may be applied to the 30, 40, and 50 Hz markers. Together, plots A and F show the accurate Fourier transform response to a windowed periodic sinusoid that ends on the period.

In plot B. pointer (24) indicates that the sampling of a 10 Hz waveform with a window that is extended beyond a single period. The corresponding DFT in plot G shows two potential misinterpretations. The first misinterpretation is indicated by pointer (25); it indicates the presence of a spectral component at 9 Hz; this is due to the change is spectral resolution due to the over sampling. Pointer (26) indicates that there exists a second spectral component of 18 Hz which would not make sense seeing there is only one wave drawn in plot B (24). Hence the misinterpretations come as a result of the misunderstanding that a Fourier transform finds true spectral content of a non-periodic waveform but when it is used in this way caution must be used in the interpretation.

Plot C shows a window of four contiguous and complete 10 Hz sinusoids consisting of 400 samples. The corresponding DFT in plot H shows pointer (27) indicating the only spectral component greater than zero magnitude is 10 Hz. Plots D and E both show periodic waveforms but they are not periodic sinusoids. Plot D shows a (non-stationary) on/off state and Plot E shows a (non-stationary) amplitude change of state. Each of the corresponding DFTs show the presence of spectral components in addition to the 10 Hz as indicated by points (28), (29), (210), and (211). The DFTs simply show which spectral components are needed to reconstruct the time domain plot for waveforms that are not stationary nor periodic across the window with respect to pure sinusoids.

FIGS. 3 and 4 show how a TF Spectrogram may be visualized. FIG. 3 shows two plots. The top plot (31) shows five seconds of an EEG recorded at 19,200 samples/second. The x-axis is labeled in time. The bottom plot (32) is a spectrogram of the EEG in (31) calculated with a sliding window size of 19,200 pts with 90% overlap, resulting in 40 windows. The spectrogram is comprised of several concatenated short time Fourier Transforms (STFT). The scale (33) indicates a normalized logarithmic measure of power in the STFTs ranging from low power, at −4, to high power, at 2. Note the y-axis indicates Frequency ranges from 0 to 1000 Hz and, based on the window selection, there is a 1 Hz resolution. A spectrogram is also commonly referred to as a Time-Frequency (TF) plot. There does not appear to be any standout spectral components.

FIG. 4 is the same as FIG. 3 except that the y-axis, representing frequency, now shows a range of 0-40 Hz, the more common range studied and published in the literature. Pointers 41, 42, and 43 correspond in definition to pointers 31, 32, and 33 of FIG. 3. The patches of white dominating the 0-10 Hz range indicates higher power in those frequency ranges compared to higher frequencies. In both figures there is an appearance of smearing across the portions of the 40 windows of spectrograms. Clarity of spectral resolution depends heavily on the experience of choosing a window length, how much to overlap consecutive windows, and if thresholding is applied, then what threshold to power level should be applied to all the TF windows simultaneously and yet retain meaningful interpretability. Many of these issues are simply derived from the various non-periodic windowing effects as demonstrated with FIG. 2.

What is needed, therefore, is a method that does not use DFT techniques. The method should concentrate on isolating individual frequency components where said frequency component starts from a resting state, lasts for at least one cycle (one period), and then returns back to a resting state over an integral multiple of the period for that frequency. The method should rely on the ability to isolate a single cycle of sinusoid within the EEG that maintains a shape consistent with a standard model of a sinusoid. In other words the method should be able to search for the presence of a stationary sinusoid on the period. The method must be able to correctly identify in time, the occurrences of 0 degrees (in-phase) or 180 degrees (opposite-phase) phase alignment.

DOCUMENTS CONSIDERED BEING RELEVANT

Reference Patents

U.S. Pat. No. 3,724,455A, 1973 Apr. 3, P Unger, Cardiac Warning Device.
U.S. Pat. No. 3,841,309, Oct. 15, 1974, Salter et al, Method of Analyzing Cerebral Electrical Activity.
U.S. Pat. No. 4,579,125, Apr. 1, 1986, Strobl et al., Real-Time EEG Spectral Analyzer.
U.S. Pat. No. 4,683,892, Aug. 4, 1987, Johansson et al., Method and Apparatus for Conducting Brain Function Diagnostic Test.
U.S. Pat. No. 5,730,146, Mar. 24, 1998, Itil et al., Transmitting, Analyzing, and Reporting EEG Data.
US 2007/0161919 A1, Jul. 12, 2007 DiLorenzo, Methods and Systems for Continuous EEG Monitoring.
U.S. Pat. No. 8,666,484 B2, Mar. 4, 2014, Nierenberg et al. Method and System for Displaying EEG Data.
US 2014/0323898 A1, Oct. 30, 2014, Purdon et al., System and Method for Monitoring Level of Dexmedatomidine-Induced Sedation.
US 2014/0323897 A1, Oct. 30, 2014, Brown et al., System and Method for Estimating High Time-Frequency Resolution EEG Spectrograms to Monitor Patient State.
U.S. Pat. No. 9,113,801 B2, Aug. 25, 2015, DiLorenzo, Methods and Systems for Continuous EEG Monitoring.
WO 2015/130955. 3 Sep. 2015, Kuzniecky, Minimally Invasive Subgaleal Extra-Cranial Electroencephalography (EEG) Monitoring Device.

Reference Papers and Private Conversations

Mr. Randall King, RADAR specialist, Avondale Shipyards, 1995, Conversation on Time Domain Reflectometry and Voltage Standing Wave Ratio.
Ramesh Srinivasan, Don M. Tucker, Michael Murias, Estimating the spatial Nyquist of the human EEG, *Behavior Research Methods, Instruments, & Computers*, 1998, 30 (1), 8-19.
Dr. George Smith, Scientist NRL-Stennis, 2000, Conversation on channel order selection in blind deconvolution of period waveforms.
Dr. Sean Chapin, University of New Orleans, 2002, Conversation on using Toeplitz matrix in null-space.
Professor George Ioup, University of New Orleans, 2002, "Remember, df= . . . ".
O. Dressler, G. Schneider, G. Stockmanns and E. F. Kochs, *Awareness and the EEG power spectrum: analysis of frequencies*, British Journal of Anaesthesia 93 (6), 2004.
Matell, M. S., Meck, W. H., *Cortico-striatal circuits and interval timing: coincidence detection of oscillatory processes*, Cogn. Brain Res. 21 (2), 2004.
Buhusi, C. V., and Meck, W. H., *What makes us tick? Functional and neural mechanisms of interval timing*, Nat. Rev. Neurosci. 6, 2005.
Elena Urrestarazu, Rahul Chander, Francois Dubeau and Jean Gotman, *Interictal high-frequency oscillations (100^500 Hz) in the intracerebral EEG of epileptic patients*, Brain (2007), 130, 2354-2366.
Mr. David Furford, AFRL, Rome, N.Y., 2007, Conversation on technical limitations of Nyquist.
Jean Gotman, *High frequency oscillations: The new EEG frontier*, Epilepsia, 2010 February.
David Hsu, Murielle Hsu, Heidi L. Grabenstatter, Gregory A. Worrell, and Thomas P. Sutula, *Time-frequency analysis using damped-oscillator pseudowavelets: application to electrophysiological recordings*, J Neurosci Methods. 2010 Dec. 15.
Madame Annette Plante, SUNY Potsdam, N.Y., 2011, Conversation Parkinson's Disease. Catalin V. Buhusia, Sorinel A. Oprisan, *Time-scale invariance as an emergent property in a perceptron with realistic, noisy neurons*, Behavioral Processes, 95, 2013.
David Hsu, Murielle Hsu, Heidi L. Grabenstatter, Gregory A. Worrell, Thomas P. Sutula, *Characterization of high frequency oscillations and EEG frequency spectra using*

*the damped-oscillator oscillator detector (DOOD)*, NIH R01-25020 and NIH R01-NS63039-01, arXiv:1309.1086, 4 Sep. 2013.

Mr. George Akmon, Dallas, Tex., 2014, Conversation on visualization technique.

Bo Shen, Zuo-Ren Wang and Xiao-Ping Wang, *The Fast Spiking Subpopulation of Striatal Neurons Coding for Temporal Cognition of Movements*, Frontiers in Cellular Neuroscience, 15 Dec. 2017.

Miguel Navarrete, Jan Pyrzowski, Juliana Corlier, Mario Valderrama, Michel Le Van Quyen, *Automated detection of high-frequency oscillations in electrophysiological signals: Methodological advances*, Journal of Physiology— Paris•February 2017.

Liu, Li Ma, Shou-Zen Fan, Maysam F. Abbod, Qingsong Ai, Kun Chen, and Jiann-Shing Shieh, *Frontal EEG Temporal and Spectral Dynamics Similarity Analysis between Propofol and Desflurane Induced Anesthesia Using Hilbert-Huang Transform*, Hindawi BioMed Research International, Volume 2018, Article ID 4939480.

Thomschewski A, Hincapié A-S and Frauscher B, *Localization of the Epileptogenic Zone Using High Frequency Oscillations*, Front. Neurol., 12 Feb. 2019.

Newson J J and Thiagarajan T C, *EEG Frequency Bands in Psychiatric Disorders: A Review of Resting State Studies*, Front. Hum. Neurosci. 12:521., 9 Jan. 2019.

Dr. Edmond Rusjan, SUNYIT, Utica, N.Y., May, 2019, Conversation on the subtle limitations of the Finite Fourier Transform.

Dr. Andrew Noga, Griffiss Institute, Rome N.Y., May, 2019. Conversation on the ABC's of reference point alignment for the SPSF matrix.

Reference Books

Sid Deutsch and Alice Deutsch, *Understanding the Nervous System, An Engineering Perspective*, IEEE Press, Piscataway, N.J., 1993.

Ronald N. Bracewell, *The Fourier Transform and Its Applications*, McGraw-Hill, 1986.

Todd K. Moon and Wynn C. Stirling, *Mathematical Methods and Algorithms for Signal Processing*, Prentice Hall, Upper Saddle River, N.J., 2000.

Richard Lyons, *Understanding Digital Signal Processing*, Prentice Hall, 1986.

Wim Van Drongelen, *Signal Processing for Neuroscientists, a Companion Volume*, Elsevier, 2010.

Michael Weeks, *Digital Signal Processing, Using Matlab and Wavelets*, Infinity Science Press, 2007.

A. Jensen, A. la Cour-Harbo, Ripples in Mathematics, The Discrete Wavelet Transform, Springer, 2003.

BRIEF SUMMARY OF THE INVENTION

The present invention is directed to a system, comprising of an electrode and a device to passively sense and record the electrical activity of the brain, where the recording is referred to as an electroencephalogram (EEG), and time domain signal processing software to analyze the recording. The main aspect of the invention is the software-based method of searching through the time series for existences of a single period of a single frequency over a set of preselected frequencies. The SPSFs are motivated by the combined concepts of individual Striatal Beat Frequencies (SBF) used to model cortical neuron activity, Frequency Domain Reflectometry used to study Voltage Standing Wave Ratios (VSWR), Geophysics Seismograms, and the ghosting effects of multipath passing through periodic sinusoids. By focusing on the search for conceptualized SBFs as manifested through the injection of individual SPSFs, the method while not professing to be perfect will mitigate errors associated with windows of time-frequency spectrogram approaches that trap spectral components in a non-periodic way.

The method being presented is only now practical to implement due to the vast improvements in high performance computing (HPC) speeds. HPCs allow for a much more detailed search for individual spectral components, using one SPSF component at a time, in contrast to the legacy Discrete Fourier Transform-based Time-Frequency (TF) spectrogram approach, which is admittedly order of magnitudes faster in processing, but which is inevitably prone to intractable error since it calculates all spectral components at one time from sampled EEG points of a never changing window size.

This invention focuses on system software that constructs a basis of single-period single-frequency (SPSF) sinusoids according to a selected sampling rate. The software utilizes said basis throughout the EEGs. A basis SPSF sinusoid is produced by software that produces a set of discrete points making up one cycle, or one period, of a sinusoid with a selected frequency component less than or equal to the sampling rate. For example, with a recording sampling rate of 19,200 points per second, an SPSF sinusoid for a frequency component of one cycle per second, or one hertz, would consist of 19,200 points; an SPSF sinusoid based on two hertz would consist of 9600 points; an SPSF for three hertz would contain 6400 points; and so on. Thus it should be specifically observed that successive SPSF windows lengths are generally of different sizes, the exceptions coming from the limitations of discrete sampling, which again, is a reminder of the uncertainty principle. Once a specific SPSF (for a specific frequency) is formed the SPSF is matched to a set of contiguous points in the EEG. From this matching of sampled points a correlation coefficient is calculated. Then, the SPSF is shifted forward in time by one sample point to obtain the next matching of sample points between it and the EEG whereupon another correlation coefficient is calculated. The process continues throughout the EEG recording for each individual SPSF of interest. For consistency in visualization the first SPSF chosen is for the frequency of 1 Hz. Thus the length of the SPSF is 19,200 points. The center of this SPSF is set at the 9,600 sample. This is referred to as the center point sample number and this is used as point of alignment for all other SPSFs. For example, for a 5 Hz SPSF, the number of samples generated is 3,840. Its center point is then set at 1920. Now when calculating a correlation coefficient with the initial 1 Hz wave, with its known center point sample number, the center point sample number of the 5 Hz SPSF is first aligned in the EEG with the 1 Hz center point sample number (1920 points to the left and 1919 points to the right of the 1 Hz center point sample number) and then the correlation coefficient is calculated and recorded in a matrix that tracks the 1 Hz center point sample number. All initial SPSFs are aligned with the first 1 Hz center point sample number indicated. Then, all correlation coefficients are calculated against the EEG, one SPSF at a time. Then, the center point of the 1 Hz SPF is moved ahead one sample and along with it the remaining SPSFs, whereupon the next set of calculations are carried out. In this way it is natural to form a matrix where the rows of the matrix identify the SPSF used to produce the correlation coefficient and the columns identify where the center point sample number of the 1 Hz wave was placed within the EEG.

The well-known Nyquist frequency criterion suggest that frequency selections are limited ½ the sampling rate. At a sampling rate of 19,200 samples per second this would suggest the highest frequency to analyze would be 9,600 Hz. For this invention, the highest frequency analyzed has been restricted to not exceed one-tenth the sampling rate.

In essence, the SPSF method searches for existence and (thus non-existence) of individual frequency components using a bank of individual SPSF windows calculated on the interval of [0:P−1], where P is the number of discrete points making up the interval based on the chosen frequency. Also, the visualization put forth on the display is based on a control of a threshold of calculated correlation coefficients. While this method professes to detect evidence of the conceptualized SBF existence and behaviors thereof, this method does not in any way profess to identify any measure of health of the brain's electrical activity with respect to the behaviors. This method should be thought of as an exploitation of spectral content in the way of which frequency is found and where in the EEG it is found.

The process is not concerned with extracting phase at each instant in time. Instead, by employing a threshold on the correlation coefficient matrix, the process is limited to identifying the peak positioned match, at zero degrees phase shift, of the base SBSF element being searched for.

BRIEF DESCRIPTION OF THE SEVERAL VIEWS OF THE DRAWING

FIG. 6 demonstrates the basis for the method of the invention from the second of two points of view; it is based on the point of view of filling in the column entries of a matrix. In the top plot, pointer (61) indicates 30,000 samples from the EEG in FIG. 4 (41). Also, there is a series of six SPSF sinusoids. Three of the SPSFs are labeled (62), (63), and (64) which correspond to 1 Hz, 2 Hz, and 3 Hz. Three additional SPSFs are plotted (4 Hz, 5 Hz, and 6 Hz) but are not labeled due to spacing. The one Hz SPSF sinusoid, (62), consists of 19,200 samples due to the EEG sampling rate of 19,200; it starts at the beginning of the EEG and ends at sample number 19,200. The center point sample number is indicated by pointer (65) and is located at sample number 19,200/2=9,600. The remaining SPSFs are centered on (65) as well. A correlation coefficient is produced between the each SPSF and the corresponding section of the EEG; for this example there are six produced in all. Pointers 67 and 68 work together to show row column positioning in the bottom figure labeled as a matrix of correlation coefficients. Pointer (66) in conjunction with (65) points to the first column of the matrix. Pointer 67 is pictured as a bracket that points to SPSFs labeled as 1 Hz through 6 Hz. These SPSFs indicate the row numbers of the matrix. The six correlation coefficients that are calculated are placed in the first six rows of the first column; this is indicated by the six colored boxes in the matrix. Additional entries to the matrix are calculated by correlating higher frequency SPSFs against the EEG and placing those results in the corresponding rows or by shifting the center point of the set of SPSFs one point to the right, calculate the set of correlation coefficients for each SPSF/ EEG pair, and then placing the results into the second column, and so on.

FIG. 8—FIG. 7 has two plots. The top plot is the same plot as in (71). The bottom plot (82) shows the matrix of entries from (72) after a threshold was put in place. Any entry of the matrix which is between −0.75 and 0.75, (not inclusive), is set to the color represented on color bar (83) as 0. The entries that remain take on the appearance of lighter and darker, corresponding to matrix entries that are either greater than or equal to 0.75 (>=0.75) or less than or equal to −0.75 (<=−0.75). This is done to better visualize a contrast, within the confines of grayscale imaging, between centered SPSFs that are highly correlated with the EEG, (negatively or positively), and SPSFs which are not.

FIG. 14 is split into two parts 14*a* and 14*b*.

FIG. 15*a* shows EEG sample points 78,001 to 80,000 (2,000 pts), taken from the last 2,000 points of FIG. 11 (111). FIG. 15*b* plots four individual rows of CCs taken from FIG. 11 (112), corresponding to the 2,000 center point sample numbers and four SBSF elements drawn from the commonly studied bands of (relatively) low frequencies: 2 Hz (Delta) wave, 5 Hz (Theta) wave, 10 Hz (Alpha) wave, and 25 Hz (Beta) wave. FIG. 14*c* plots four individual rows of CCs, corresponding to the 2,000 center point sample numbers and four SBSF elements from the less-commonly studied bands of (relatively high) frequencies, referred to as 'ripples': a 100 Hz wave, a 300 Hz wave, a 500 Hz wave, and a 800 Hz wave. Consistent with previous scales, all CCs between −0.75 and 0.75 have been set to zero; any non-zero point shown is either (>=0.75) or (<=−0.75). Pointers (151) through (158) indicate a neighborhood of samples, namely center point samples 78,600 to 79,000, to compare and contrast the CC responses among the eight selected frequencies.

DETAILED DESCRIPTION OF THE INVENTION

This section will describe the details for forming a matrix of calculated correlation coefficients where said calculation is a function of a single period (cycle) of a single frequency (SPSF) sinusoid and a time domain position within a recorded EEG. All actions described herein are executed automatically through stored computer instructions; all input EEGs, the bank of Single-Period Single-Frequency (SPSF) sinusoids, and the correlation coefficient output matrix are stored in memory and then are called from memory as needed to execute and store the calculations.

Figure 1:
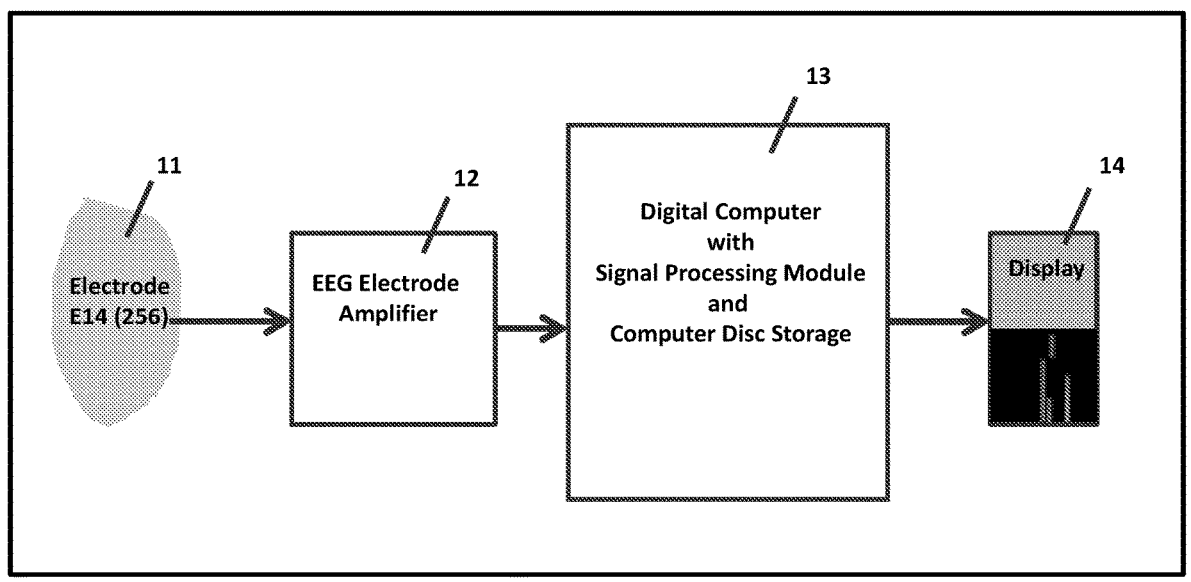
FIG. 1 is a system diagram for capturing and displaying an electroelectroencephalogram (EEG) and for displaying transformations of said EEG for purposes of analysis. The system includes (11) the EEG electrode, specifically E14 of a 256 node cap, that is attached to the scalp, (12) an electrode signal amplifier, (13) a digital computer equipped to execute code from a signal processing module and store information, and (14) a display to observe the signal in its raw form and any transformations of the raw signal.
Figure 2:
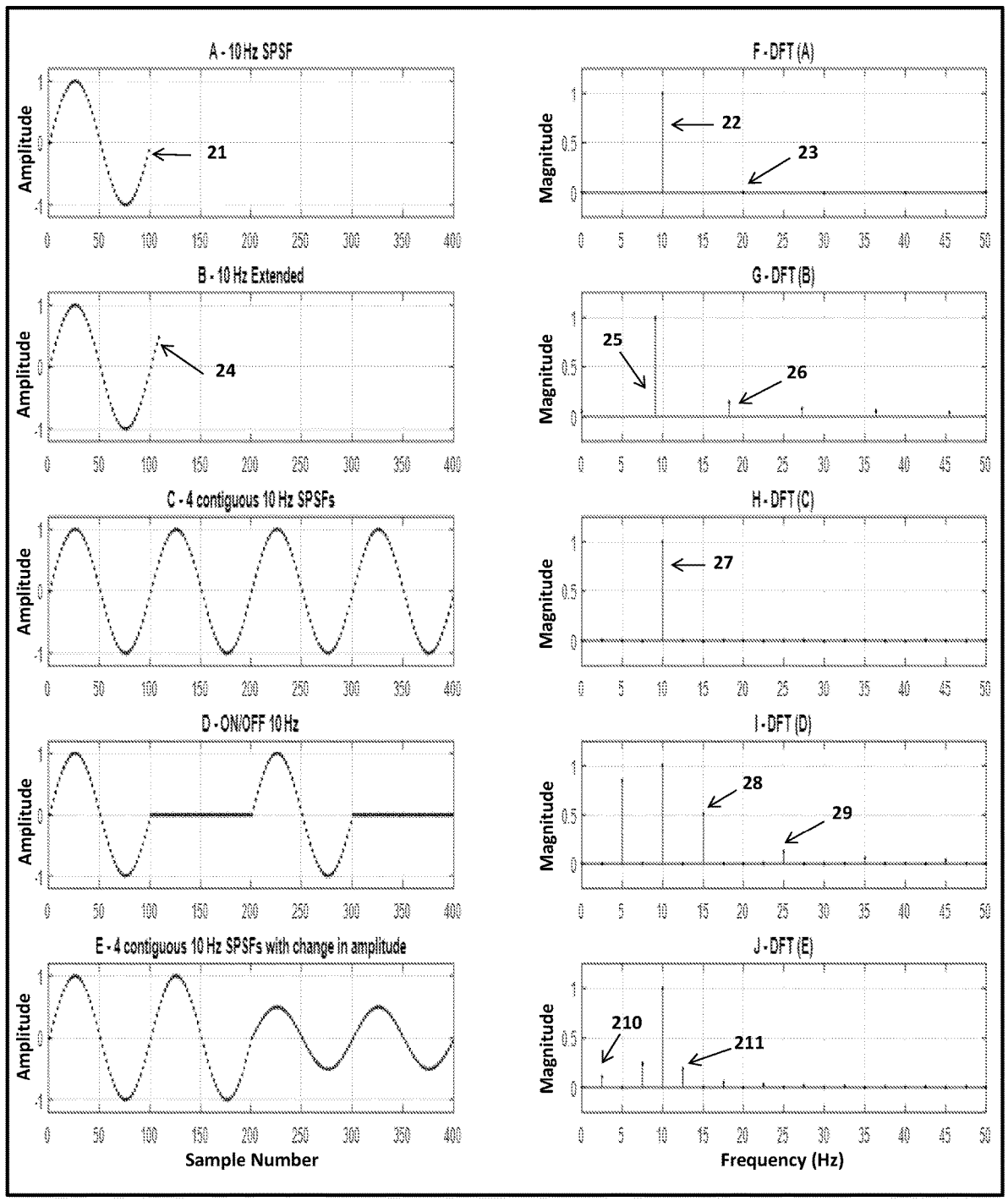
FIG. 2 is an example to show the limitations to making accurate appraisals of spectral content from windowed waveforms. Plots A-E show different applications of a 10 Hz sinusoid. Pointers (21) and (24) indicate the end of a single period and the extension of a single period correspondingly. Plots (F-J) are corresponding DFT of plots (A_E). Pointers (22) and (27) indicate the presence of a single 10 Hz sinusoidal component and (23) indicates the absence of a spectral component. The remaining pointers (25), (26), (28), (29), (210), and (211) all indicate the presence of spectral components other than 10 Hz.

For patients who require an analysis of the electrical activity of their brain, a typical non-invasive approach is to record an electroencephalogram (EEG) in order to perform a time-domain analysis of the signal. FIG. 1 shows a system that records an EEG. Pointer (11) points to an electrode that is placed on the scalp. Where the electrode is placed, is a function of an internationally recognized electrode cap positioning scheme. Pointer (11) shows that for a 256 electrode cap mapping, position E14 is the source for passively collecting electrical brain activity. The electrical activity is passed on to an amplifier, (12), which then sent to a computer that is programmed with a signal processing module and computer disc storage. Results from the signal processing are sent to a display for analysis.

From a conceptual standpoint, the presented invention searches for the presence of cortical neurons firing in an oscillatory manner. The oscillations are referred to as Striatal Beat Frequencies (SBF). The present invention models these SBFs as SPSF sinusoids and it is the application of said invention that executes a search for the presence, and duration thereof, said oscillations.

Figure 5:
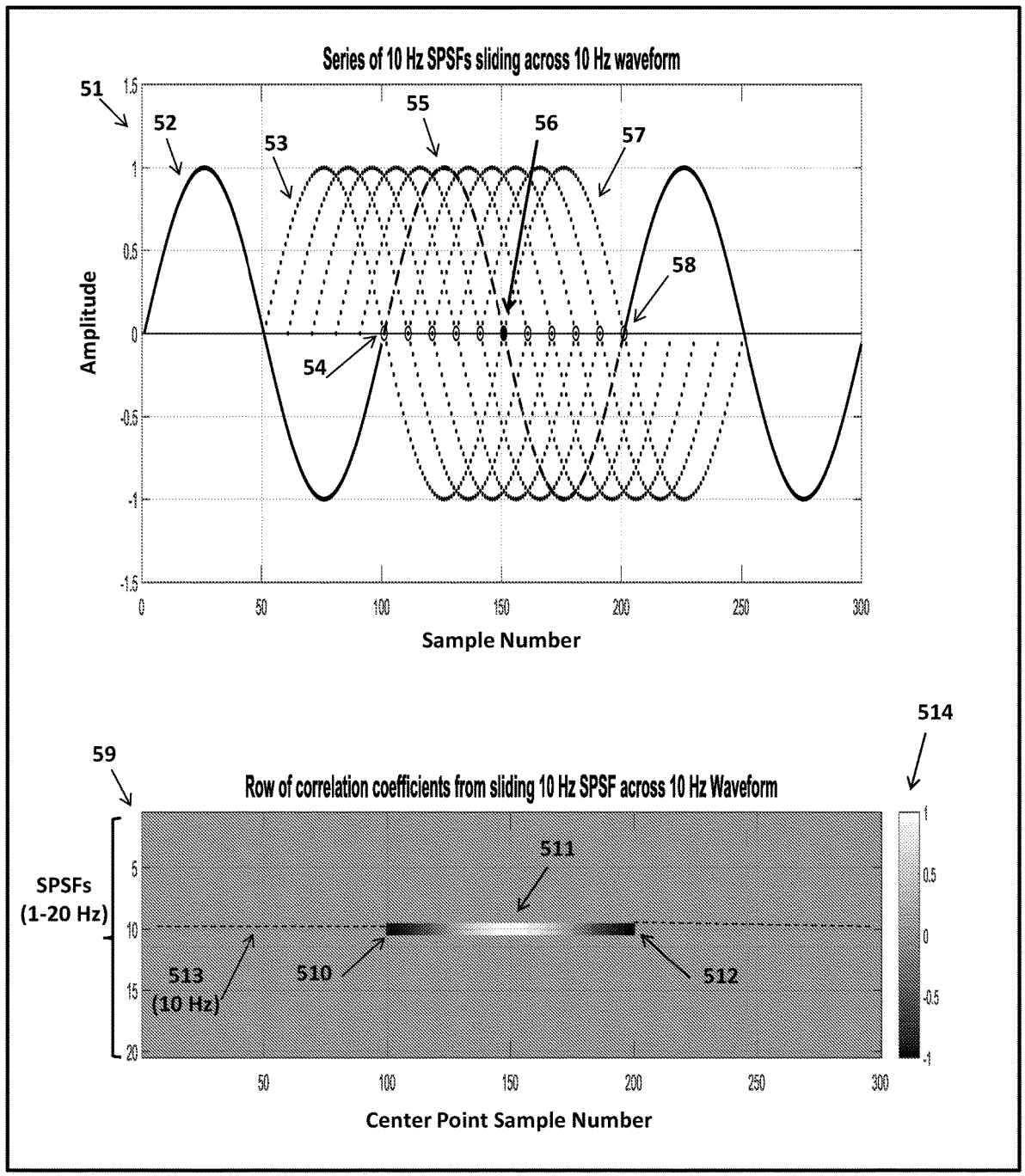
FIG. 5 demonstrates the basis for the method of the invention from the first of two points of view; it is based on the point of view of filling in the row entries of a matrix. The top plot, (51), shows a series of 10 Hz sinusoids generated with a sampling rate of 1000 samples/second. This defines the number of samples in one cycle, or one period, to consist of 100 samples. Pointer (52) indicates a sinusoidal signal consisting of three concatenated 10 Hz sinusoids where sample numbers 0 to 99 shows a solid line, sample numbers 100 to 199 show a dashed line, and sample numbers 200 to 299 show a solid line; this is done in this to emphasize a contrast between (51) the remaining sinusoids. Pointer (53) indicates a 10 Hz single-period single frequency (SPSF) sinusoid. The SPSF starts at sample number 50 and ends at sample number 149. Pointer (54) indicates the center point sample number of this SPSF with a small circle drawn in. The 100 samples of (53), centered on sample number 100, are exactly 180 degrees out of phase with the corresponding 100 points from the signal (52); this results in a calculated correlation coefficient value of −1.0. As the 100 points of (53) are shifted to the right, one point at a time, so does the center point sample number indicator (54). At each shift a new correlation coefficient is calculated. To reach the SPSF indicated by (57) one hundred shifts would need to take place. Correspondingly the center point (54) would be shifted to (58). Several SPSFs have been drawn in to help visualize the movement every five shifts. Pointer (55) indicates the position of a shifted SPSF that is perfectly in-phase with the corresponding points from (52). Pointer (56) indicates the center point sample number of (5) is set at sample number 100. In this case the correlation coefficient is equal to 1.0. The bottom plot, (59), shows a matrix of 20×300. The '20' refers to 20 rows of SPSF ranging from 1 to 20 Hz. The '300' refers to the position of the center sample point numbers drawn from the top plot (51). There are 101 correlation coefficient numbers calculated (inclusively between (53) and (57)) with the same 10 Hz SPSF. Hence the 101 coefficients are listed in the 10$^{th}$ row of the matrix, (513), and they are contained (inclusively) between center point sample numbers 100 and 200, as indicated by pointers (510) and (512). The values of the correlation coefficients range between −1.0 and 1.0 and the color bar (514) shows the corresponding color pattern for the entries (or pixels) in the matrix. Note that in this example the signal (52) is also set to 10 Hz but to show the evolution of the correlation coefficients; (52) has nothing to do with the row selection; row selection is solely based on SPSF selection.
Figure 6:
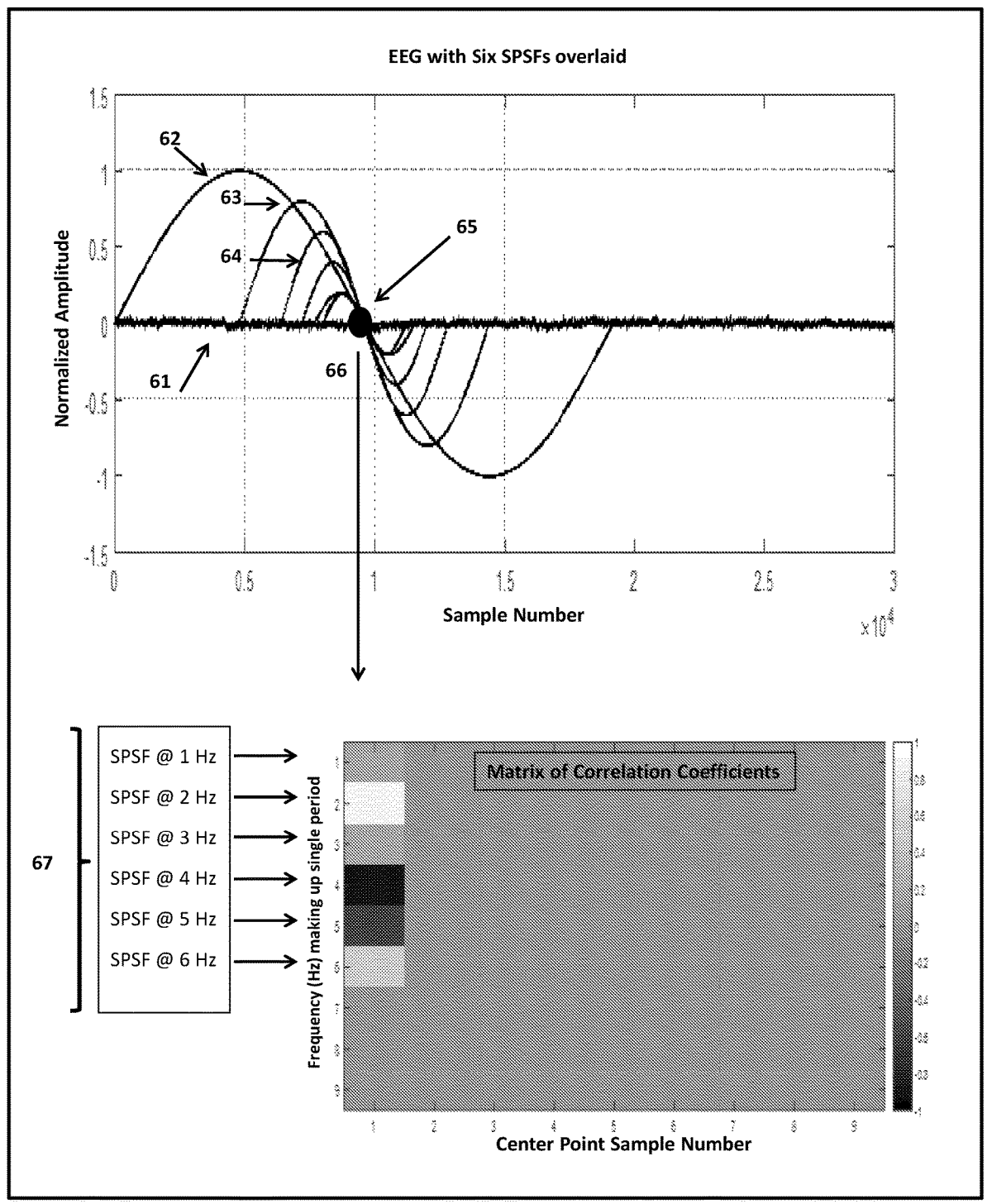

FIGS. 5 and 6 demonstrate the two base operations that are executed, using the SPSFs and the EEG, in order to acquire correlation coefficients which placed into a matrix format. The remaining figures are used to show how these two base operations are applied to a real EEG recorded as shown in FIG. 1.

FIG. 5 demonstrates the basis for the method of the invention from the first of two points of view; it is based on the point of view of filling in the row entries of a matrix with correlation coefficients calculated as a function of an SPSF and the EEG. The top plot, (51), shows a series of 10 Hz sinusoids generated with a sampling rate of 1000 samples/second. This defines the number of samples in one cycle, or one period, to consist of 100 samples. Pointer (52) indicates a signal that takes the place of an EEG for this demonstration. The signal is a sinusoidal signal consisting of three concatenated 10 Hz sinusoids where sample numbers 0 to 99 shows a solid line, sample numbers 100 to 199 show a dashed line, and sample numbers 200 to 299 show a solid line; this is done in this to emphasize a contrast between (52) the bank of SPSFs to be described next. Pointer (53) indicates the first of a series of pictured 10 Hz single-period single-frequency (SPSF) sinusoids. The SPSF starts at sample number 50 and ends at sample number 149. Pointer (54) indicates the center point sample number of this SPSF being located at sample number 100. The 100 samples of (53), centered on sample number 100, are exactly 180 degrees out of phase with the corresponding 100 points from the signal (52); this results in a calculated correlation coefficient value of −1.0. As the 100 points of (53) are shifted to the right, one point at a time, so does the center point sample number indicator (54). At each shift a new correlation coefficient is calculated. To reach the SPSF which starts at sample [point number 150, as indicated by (57), one hundred shifts would need to take place. Correspondingly the center point (54) would be shifted to center point sample number 200 as indicated by pointer (58). Additional SPSFs have been drawn in every five shifts to help visualize the movement. Pointer (55) indicates the position of a shifted SPSF that is perfectly in-phase with the corresponding points from (52). Pointer (56) indicates the center point sample number of (55) is set at sample number 100. In this case the correlation coefficient is equal to 1.0.

The bottom plot, (59), shows a matrix of dimensions 20×300. The '20' refers to 20 rows of SPSFs ranging from 1 to 20 Hz. The '300' refers to the position of the center sample point numbers drawn from the top plot (51). In this example, there are 101 correlation coefficient numbers calculated (inclusively between (53) and (57)) the sliding base 10 Hz SPSF sinusoid (53) and the signal under evaluation (52). Hence the 101 coefficients are entered in the $10^{th}$ row of the matrix, (513) and are contained (inclusively) between center point sample numbers 100 and 200, as indicated by pointers (510) and (512). The values of the correlation coefficients range between −1.0 and 1.0. The color bar (514) shows the corresponding color pattern for the entries in the matrix.

Note that in this example the signal (52) is purposely set to 10 Hz to show the evolution of the correlation coefficients between the 10 Hz base SPSF and a potential EEG with the same frequency. Note that (52) has nothing to do with the row selection; row selection is solely based on SPSF selection.

FIG. 6 demonstrates the basis for the method of the invention from the second of two points of view; it is based on the point of view of filling in the column entries of a matrix with correlation coefficients calculated as a function of a set of SPSFs centered around the same center point sample number and the EEG. In the top plot, pointer (61) indicates 30,000 samples taken from the EEG in FIG. 4 (41). Also, there is a series of six SPSF sinusoids. Three of the SPSFs are labeled (62), (63), and (64) which correspond to 1 Hz, 2 Hz, and 3 Hz. Three additional SPSFs are plotted (4 Hz, 5 Hz, and 6 Hz) but are not labeled due to spacing. The 1 Hz SPSF sinusoid, (62), consists of 19,200 samples due to the EEG sampling rate of 19,200; it starts at the beginning of the plotted EEG and ends at sample number 19,200. The center point sample number is indicated by pointer (65) and is located at sample number 19,200/2=9,600. The remaining SPSFs are centered on (65) as well. A correlation coefficient is calculated between the each SPSF and corresponding section of the EEG; for this example there are six calculations produced in all.

Pointers (66) and (67) from FIG. 6, collectively, show the row/column positioning in the bottom figure labeled as Matrix of Correlation Coefficients. Pointer (66) indicates that the first column of the matrix is aligned in time with the center point sample number as indicated by (65). Pointer (67) is pictured as a bracket that points to the row assignments for SPSFs labeled as 1 Hz through 6 Hz. These SPSFs indicate the row numbers of the matrix. The six correlation coefficients that are calculated are placed in the first six rows of the first column; this is indicated by the six colored boxes in the matrix. Additional entries to the matrix are calculated by correlating higher frequency SPSFs against the EEG and placing those results in the corresponding rows or by shifting the center point of the set of SPSFs one point to the right, calculate the set of correlation coefficients for each SPSF/EEG pair, and then placing the results into the second column, and so on.

Taking FIGS. 5 and 6 together, they show how a plurality of SPSFs, varying in frequency and in an aligned center point placement along the EEG, are used to calculate correlation coefficients that are recorded in an (SPSF correlation) matrix. This is the basis—for the remaining detailed description of the patent and accompanying figures.

Figure 7:
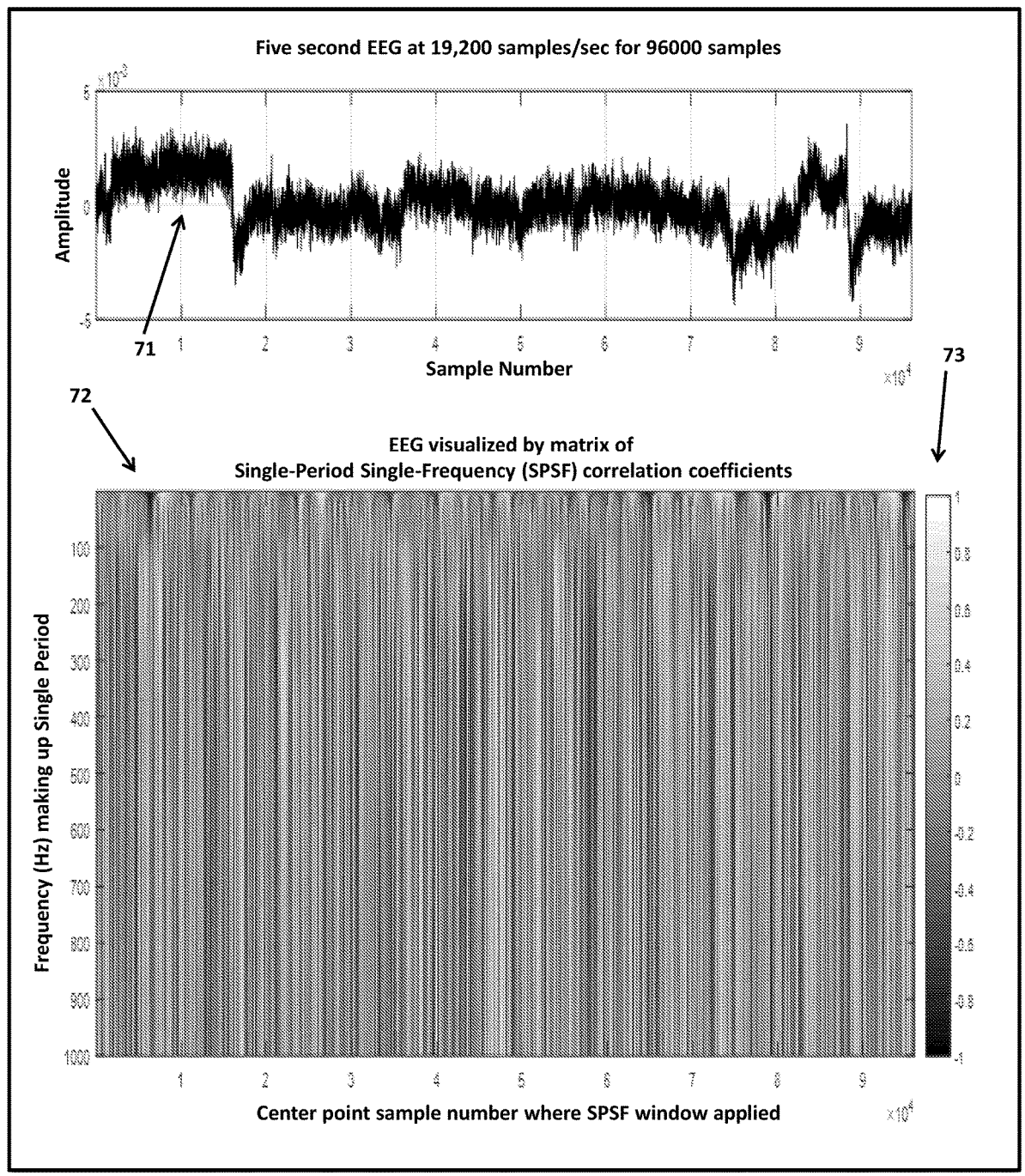
FIG. 7—There are two plots. The top plot (71) is a repeat of EEG plot (31) except that the x-axis is no longer indicates time in seconds. Instead, the x-axis now indicates sample number. Each full grid division contains 10,000 points ($10^4$). The x-axis ranges from 1 to 96,000 ($9.6 \times 10^4$). The bottom plot (72) is a matrix of correlation coefficients (CCs). The scale (73) indicates a range of −1.0 to 1.0, which reflects the normal range of a correlation coefficient. The y-axis indicates the choice of a Single-Period Single-Frequency (SPSF) element from among the bank of 1,000 elements which for the purpose of describing the invention correspond 1 to 1000 Hz. The x-axis indicates where the center point of the SPSF was placed among the 96,000 samples in (71). Note that the plot of CCs values shown in the bottom plot of FIG. 5 would be placed in the $10^{th}$ row, corresponding to 10 Hz, and from columns 101 to 200, corresponding to the center points.

FIG. 7 demonstrates the first full visualization of a real EEG with a corresponding matrix of correlation coefficients associated with the bank of SPSFs. There are two plots. The top plot (71) is a repeat of EEG plot (31) from FIG. 3 except that the x-axis is no longer indicates time in seconds. Instead, the x-axis now indicates sample number. Each full grid division contains 10,000 points ($10^4$). The x-axis ranges from 1 to 96,000 ($9.6 \times 10^4$). The bottom plot (72) is a matrix of correlation coefficients (CCs). The scale (73) indicates a range of −1.0 to 1.0, which reflects the normal range of a correlation coefficient. The y-axis indicates the row which corresponds to the choice of a Single-Period Single-Frequency (SPSF) element from among the bank of 1,000 elements, which for the purpose of describing the invention, correspond 1 to 1000 Hz. The x-axis indicates where the center point of the SPSF was placed among the 96,000 samples in (71). In effect, the 96,000 center points account for 96,000 centered windows for each of the 1000 individual SPSFs. Thus this matrix has dimensions of 1000×96,000 where each entry therein is the result of an independent calculation.

Note that the plot of CCs values shown in the bottom plot of FIG. 5 would be placed in the $10^{th}$ row of the matrix which corresponds to 10 Hz, and from columns 101 to 200 which corresponding to the center point sample numbers.

Figure 8:
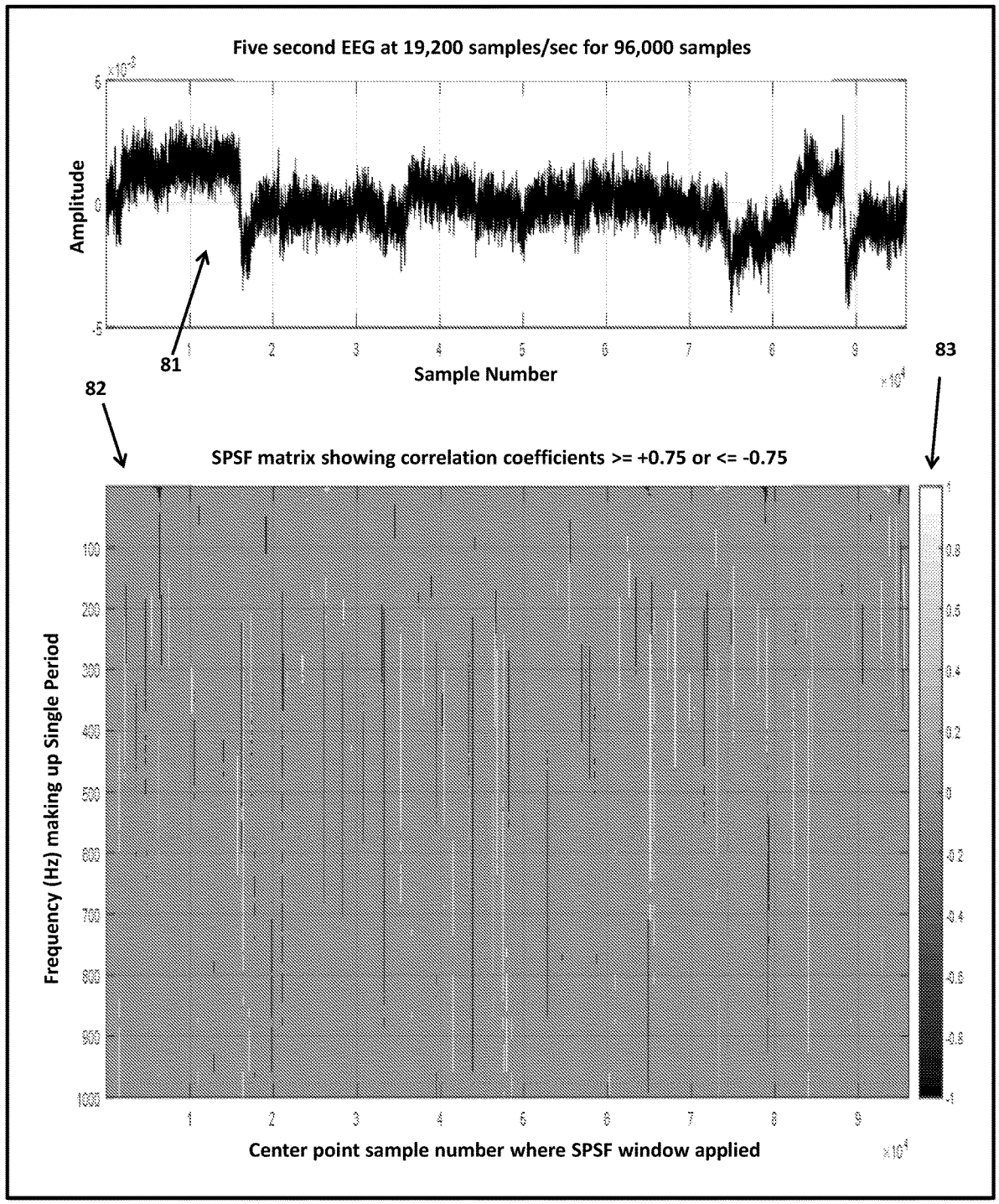

FIG. 8 is shown to demonstrate the visual effect of applying a threshold to the correlation coefficient matrix from FIG. 7. FIG. 8 has two plots. The top plot is the same plot as in (71) from FIG. 7. The bottom plot (82) shows the matrix of entries from (72) after a threshold was put in place. The threshold is set such that any entry of the matrix which is between −0.75 and 0.75, (not inclusive), is set to the color represented on color bar (83) as 0. The entries that remain take on the appearance of lighter and darker, corresponding to matrix entries that are either greater than or equal to 0.75 (>=0.75) or less than or equal to −0.75 (<=−0.75). This is done to better visualize a contrast, within the confines of grayscale imaging, between centered SPSFs that are highly correlated with the EEG, (negatively or positively), and SPSFs which are not.

Figure 3:
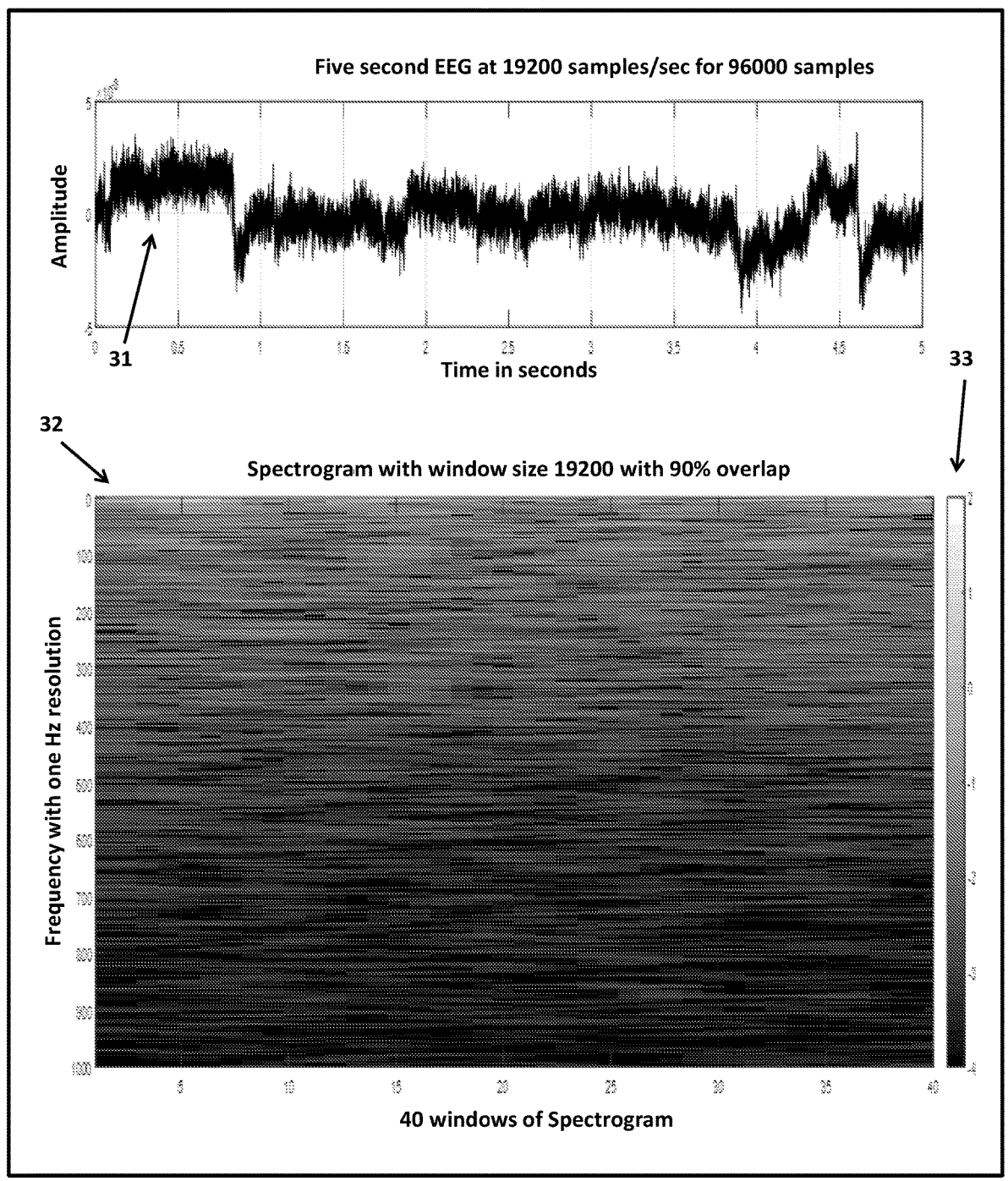
FIG. 3 shows two plots. The top plot (31) shows five seconds of an EEG recorded at 19,200 samples/second. The x-axis is labeled in time. The bottom plot (32) is a spectrogram of the EEG in (31) calculated with a sliding window size of 19,200 pts with 90% overlap, resulting in 40 windows. The spectrogram is also known as a Short Time Fourier Transforms (STFT). The scale (33) indicates a normalized logarithmic measure of power in the STFTs ranging from low power, at −4, to high power, at 2. Note the y-axis indicates Frequency ranges from 0 to 1000 Hz with a one hertz resolution. A spectrogram is also commonly referred to as a Time-Frequency (TF) plot.
Figure 4:
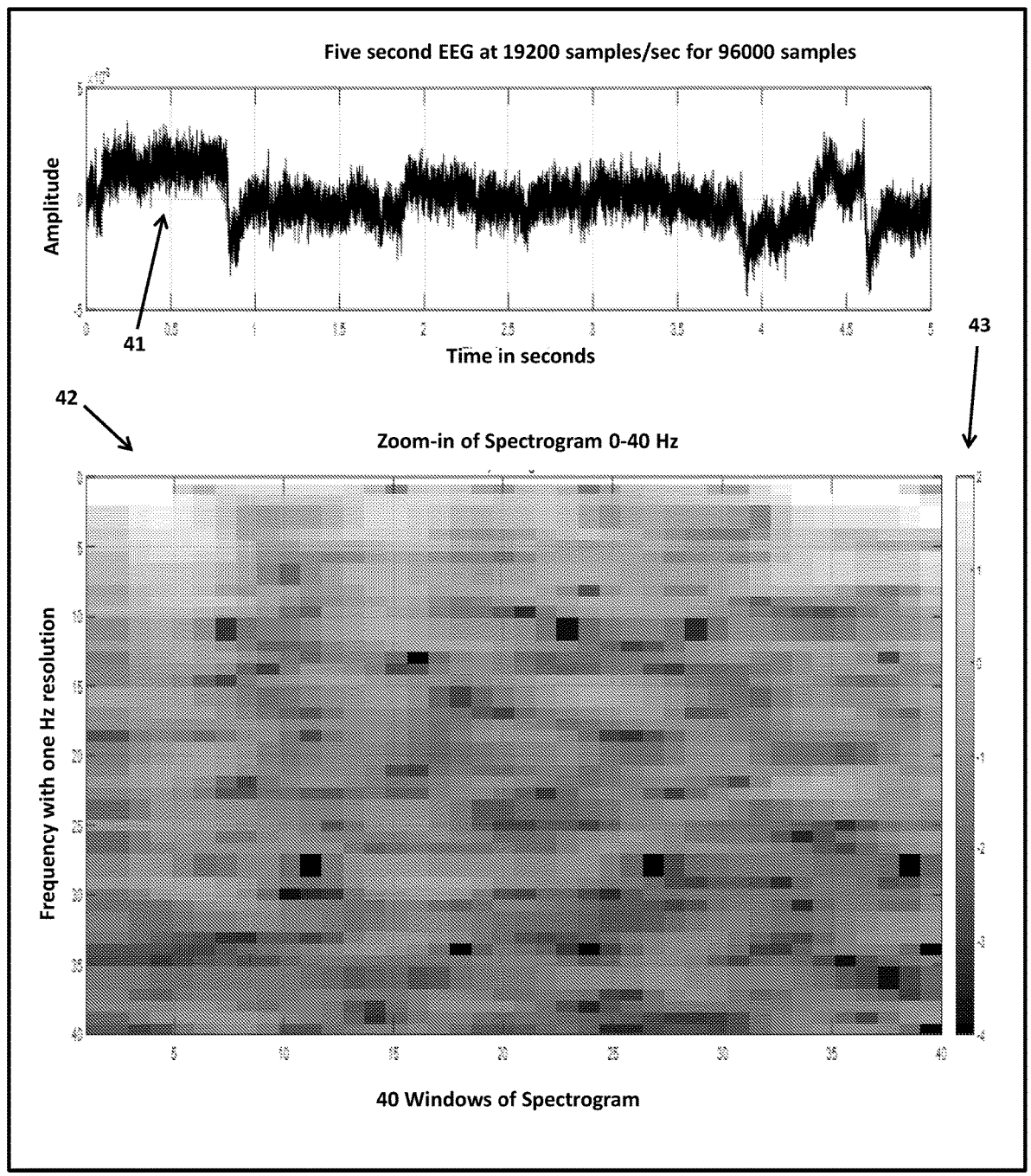
FIG. 4 is the same as FIG. 3 except that the y-axis of the TF spectrogram, (42), now shows a zoom-in range of 0-40 Hz, the more common range studied and published in the literature. The patches of white dominating the 0-10 Hz range indicates higher power in those frequency ranges compared to higher frequencies. Pointers 41, 42, and 43 correspond to pointers 31, 32, and 33 of FIG. 3.
Figure 9:
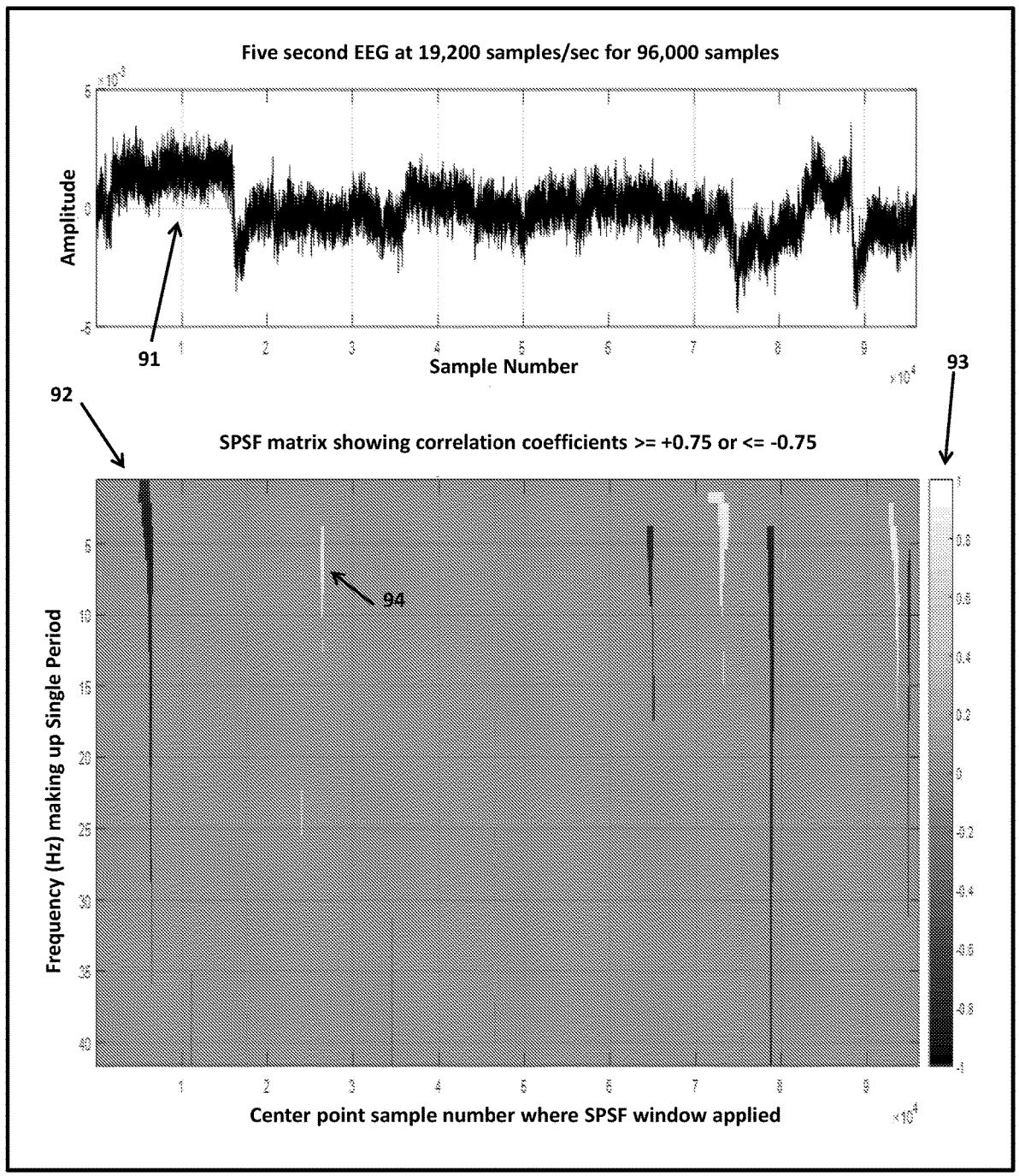
FIG. 9 is a repeat of FIG. 8 except that the y-axis of the bottom plot (92) zooms-in to SPSFs 0 to 40 Hz. Again, only CCs (>=0.75) and (<=−0.75) are shown. A patch (94) of high CC, (>=0.75) is shown to approximately lie between the SPSFs 4 Hz to 11 Hz and center point sample numbers 26000 and 27000 ($2.6 \times 10^4$ and $2.7 \times 10^4$).

The visualized matrix in FIG. 9 shows signs of smearing in the vertical direction in contrast to the horizontal smearing of the TF spectrograms shown in FIGS. 3 and 4. However, the amount of vertical smearing in the visualized SPSF matrix can be controlled by a simple change in the threshold used for displaying the correlation coefficients. FIG. 9 is a repeat of FIG. 8 except that the y-axis of the bottom plot (92) zooms-in to SPSFs 0 to 40 Hz. Again, only CCs (>=0.75) and (<=−0.75) are shown. A patch (94) of high CC values, (>=0.75), is shown to approximately lie between the rows marking SPSFs 4 Hz to 11 Hz and columns marking center point sample numbers 26000 to 27000 ($2.6 \times 10^4$ and $2.7 \times 10^4$). FIG. 9 shows the lack of highly correlated SPSFs with the EEG as indicated by the amount of entries set to 0.

Figure 10:
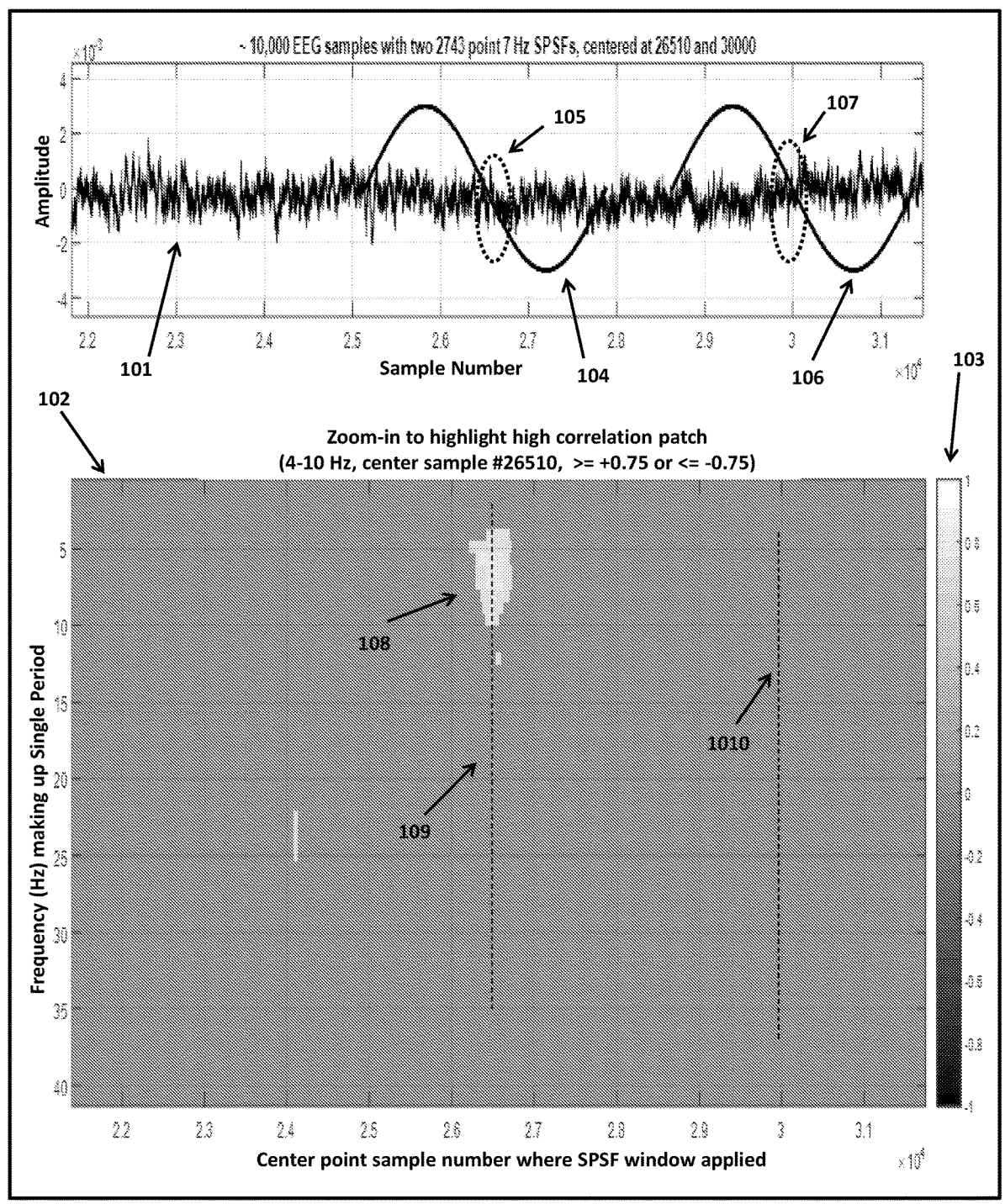
FIG. 10 is based on FIG. 9. The bottom plot (102) shows the high CC patch (108) taken from FIG. 8 (94). The y-axis still ranges from 0 to 40 Hz but the x-axis zooms-in to center point sample numbers 20,000 to 31,000. Pointers (109) and (1010) indicate the locations for center point sample numbers 26,510 and 30,000. (103) is the CC scale ranging (−1 to 1), but noting only those matrix entries (>=0.75) or (<−0.75) are shown; all other entries set to 0. The top plot (101) shows the EEG samples corresponding to the range of center point sample numbers from (102). Two 7 Hz SPSFs, (104) and (106), have been superimposed over the EEG. A 7 Hz SPSF contains 2743 samples (round: 19200/7). Pointers (105) and (107), indicate the center points in-line with (109) and (1010). Note that plot (101) should be padded to the left and right by 19200/2 points, as shown in FIG. 6; padding is not shown in FIG. 10 in order to maintain a visual alignment between the top and bottom plots.

FIG. 10 demonstrates the positioning of SPSFs among the EEG and the corresponding entries in the matrix entries that capture the highly correlated patch of entries taken from FIG. 9 pointer (94). The bottom plot (102) shows in greater detail the high CC patch (108) taken from FIG. 9 (94). The y-axis still ranges from 0 to 40 Hz but the x-axis zooms-in to center point sample numbers 20,000 to 31,000 which corresponds to nearly ½ second of time. Pointers (109) and (1010) indicate the locations for center point sample numbers 26,510 and 30,000. Pointer (103) indicates the CC scale ranging from 0.75 to 1 and from −0.75 to −1.0, while all other entries set to 0. The top plot (101) shows the EEG samples corresponding to the range of center point sample numbers from (102). Two 7 Hz SPSFs, (104) and (106), have been superimposed over the EEG. A 7 Hz SPSF contains 2743 samples (round: 19200/7). Pointers (105) and (107), indicate the center points in-line with (109) and (1010).

Note that plot (101) should be padded to the left and right by 19200/2 points, as shown in FIG. 6; padding is not shown in FIG. 10 in order to maintain a visual alignment between the top and bottom plots.

The next five figures, FIGS. 11 through 15, are used to drill deeper into the details of what the search for SPSFs provide in the way of in-phase and 180 degree out of phase detections using the thresholded correlation coefficient matrix.

Figure 11:
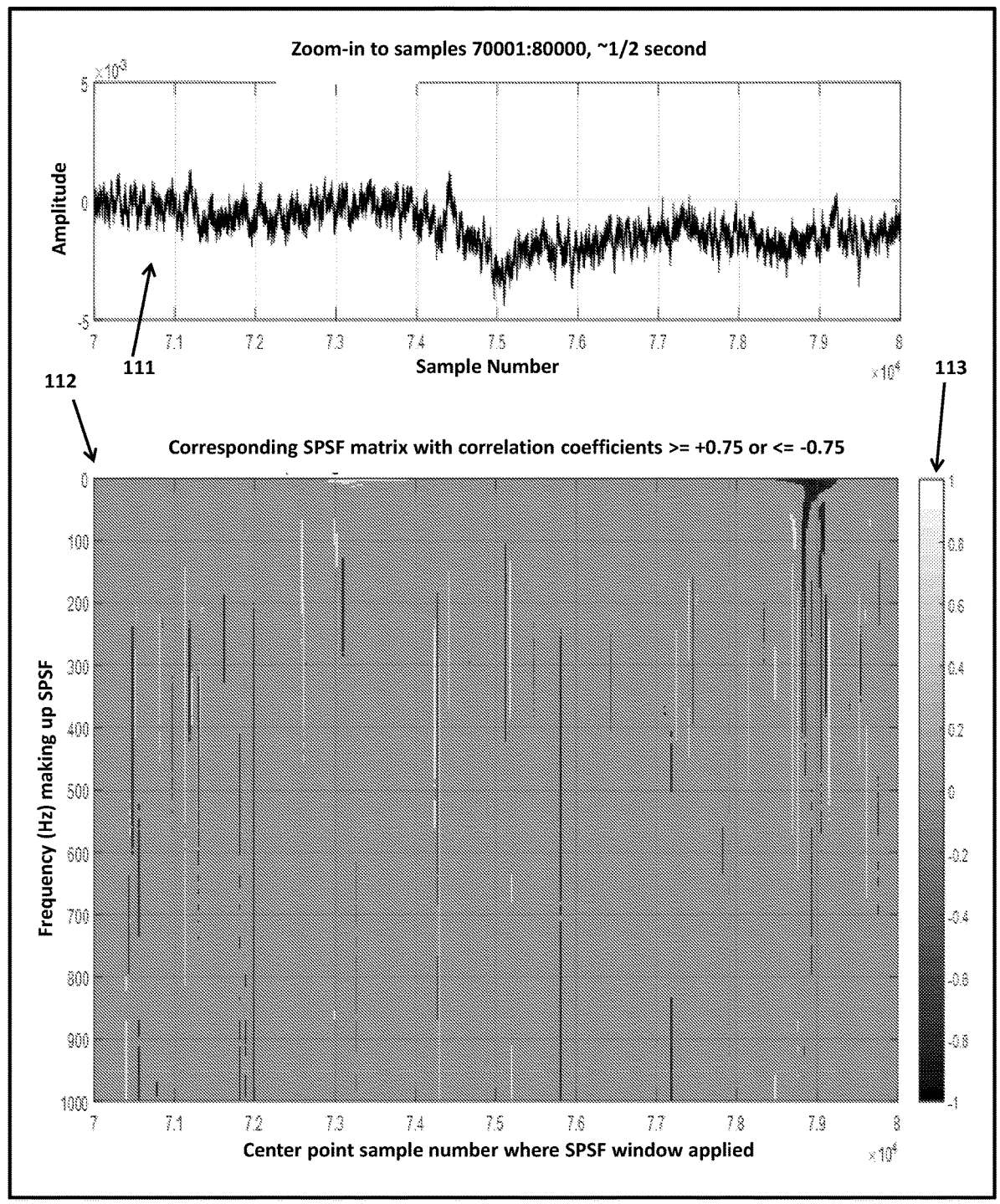
FIG. 11 shows the top plot (111) zooming-in to EEG sample numbers 70,001 to 80,000 ($7 \times 10^4$ to $8 \times 10^4$). The bottom plot (112) shows the SPSF matrix for the corresponding center point sample numbers over the full range of SPSFs, 1-1000 Hz. The scale (113) is the same as for previous scales, e.g. pointer (83), i.e., an indicator of CCs (>=0.75) or (<=−0.75). Note that 10,000 samples equates to approximately ½ second of time.

FIG. 11 shows a ½ second interval of EEG and the corresponding SPSF correlation coefficient matrix span 1000 rows of SPSF ranging from 1 to 1000 Hz. FIG. 11 shows the top plot (111) zooming-in to EEG sample numbers 70,001 to 80,000 ($7 \times 10^4$ to $8 \times 10^4$). The bottom plot (112) shows the SPSF matrix for the corresponding center point sample numbers over the full range of SPSFs, 1-1000 Hz. The color bar scale (113) is the same as for previous scales, e.g. pointer (83), i.e., an indicator of CCs (>=0.75) or (<=−0.75).

Figure 12:
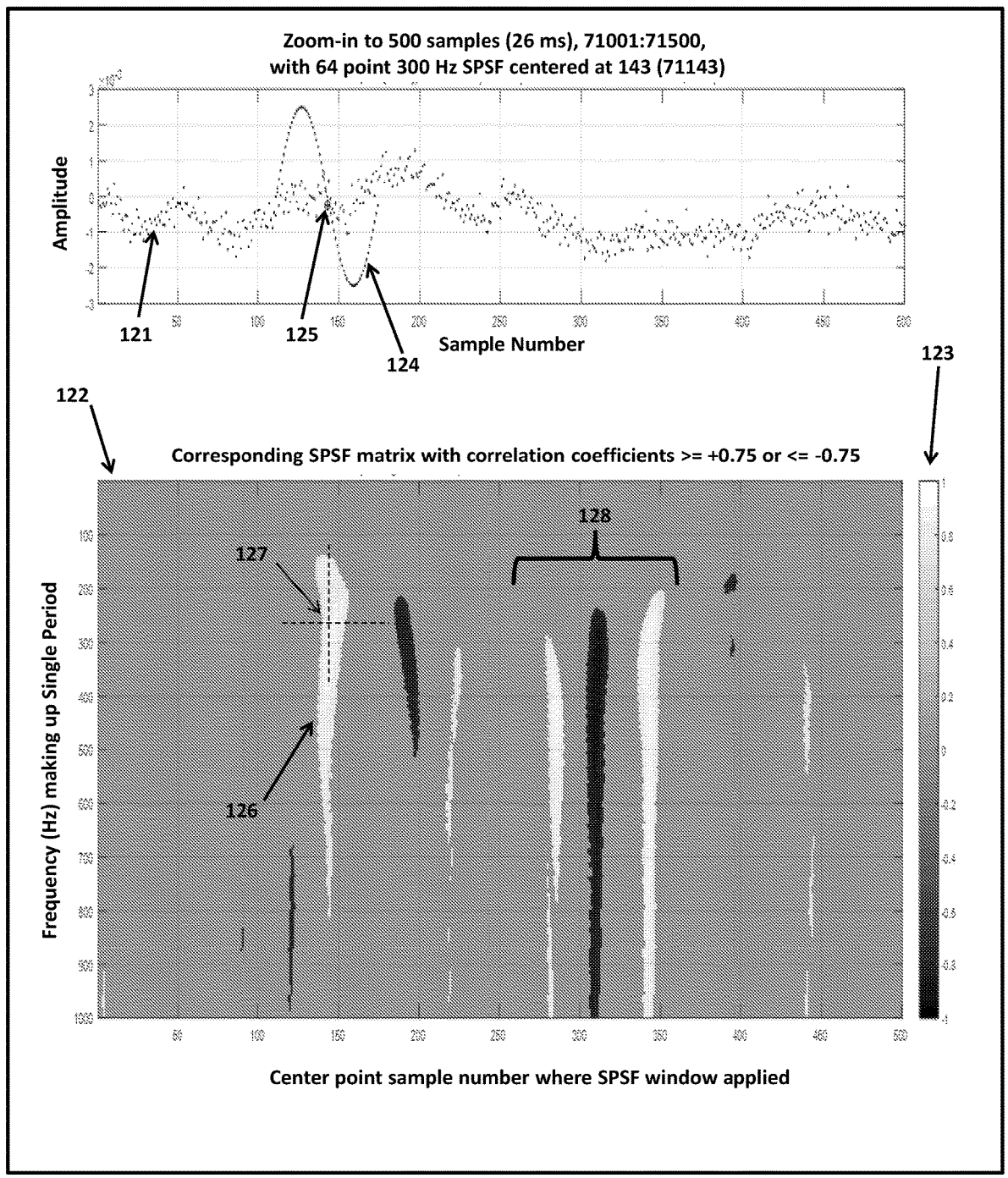
FIG. 12 has two plots. The top plot (121) shows EEG sample numbers 71001:71500 which, for ease of discussion, have been rewritten as samples 1 to 500 on the x-axis. 500 samples correspond to 26 ms of time. A 300 Hz SPSF (124) consisting of 19200/300=64 points has been superimposed over the EEG. The SPSF is centered (125) at sample number 143 (EEG sample 71,143). The x-axis of the matrix plot (122) shows the corresponding 500 center point sample numbers; the y-axis reflects the CC measures for SPSF frequencies 1 to 1000 Hz. The scale (123) ranges from (−1 to 1), but the matrix elements are set to 0 if their CC is (<0.75) and (>=0.75), as with previous figures. Pointer (126) points to a patch of matrix entries (pixels) where the cc is >=0.75. The approximate width of the patch is that of 10 samples (~0.5 ms). Pointer (127) points to the intersection of the row representing the 300 Hz SPSF and the center point sample number at 143. A series of high-low-high CC patches is indicated by pointer (128).

FIG. 12 is a zoom-in of the EEG waveform in FIG. 11. The zoom in is necessary due to the constraints of using a grayscale and the physical limitation of shows matrix entries with pixels in a generated plot. FIG. 12 has two plots. The top plot (121) shows EEG sample numbers 71001:71500 which, for ease of discussion, have been rewritten as samples 1 to 500 on the x-axis. 500 samples correspond to 26 ms of time. A 300 Hz SPSF (124) consisting of 19200/300=64 points has been superimposed over the EEG. The SPSF is centered (125) at sample number 143 (EEG sample 71,143). The x-axis of the matrix plot (122) shows the corresponding 500 center point sample numbers; the y-axis reflects the CC measures for SPSF frequencies 1 to 1000 Hz. The scale (123) ranges from (−1 to 1), but the matrix elements are set to 0 if their CC is (<0.75) and (>=0.75), as with previous figures.

Pointer (126) points to a patch of matrix entries (pixels) where the cc is >=0.75. The approximate width of the patch is that of 10 samples (~0.5 ms). Pointer (127) points to the intersection of the row representing the 300 Hz SPSF and the center point sample number at 143 The patch of correlations indicated by (126) and specifically the area encompassing pointer (127) is developed upon in greater detail in FIGS. 13 and 14.

There are two signal processing observations from the matrix shown in (122) to be noted. The first observation to note is the coupling between time of arrivals of the in-phase and 180 degree out-of-phase components of the SPSFs among the short series of high-low-high CC patches indicated by pointer (128). Pointer (128) suggests that there were two periods (cycles) of SPSFs detected in 100 samples of each other. The second observation is that this method did not detect any highly correlated interactions between the EEG and any SPSF below 100 Hz. These observations do not profess to be associated with any neurological condition.

Figure 13:
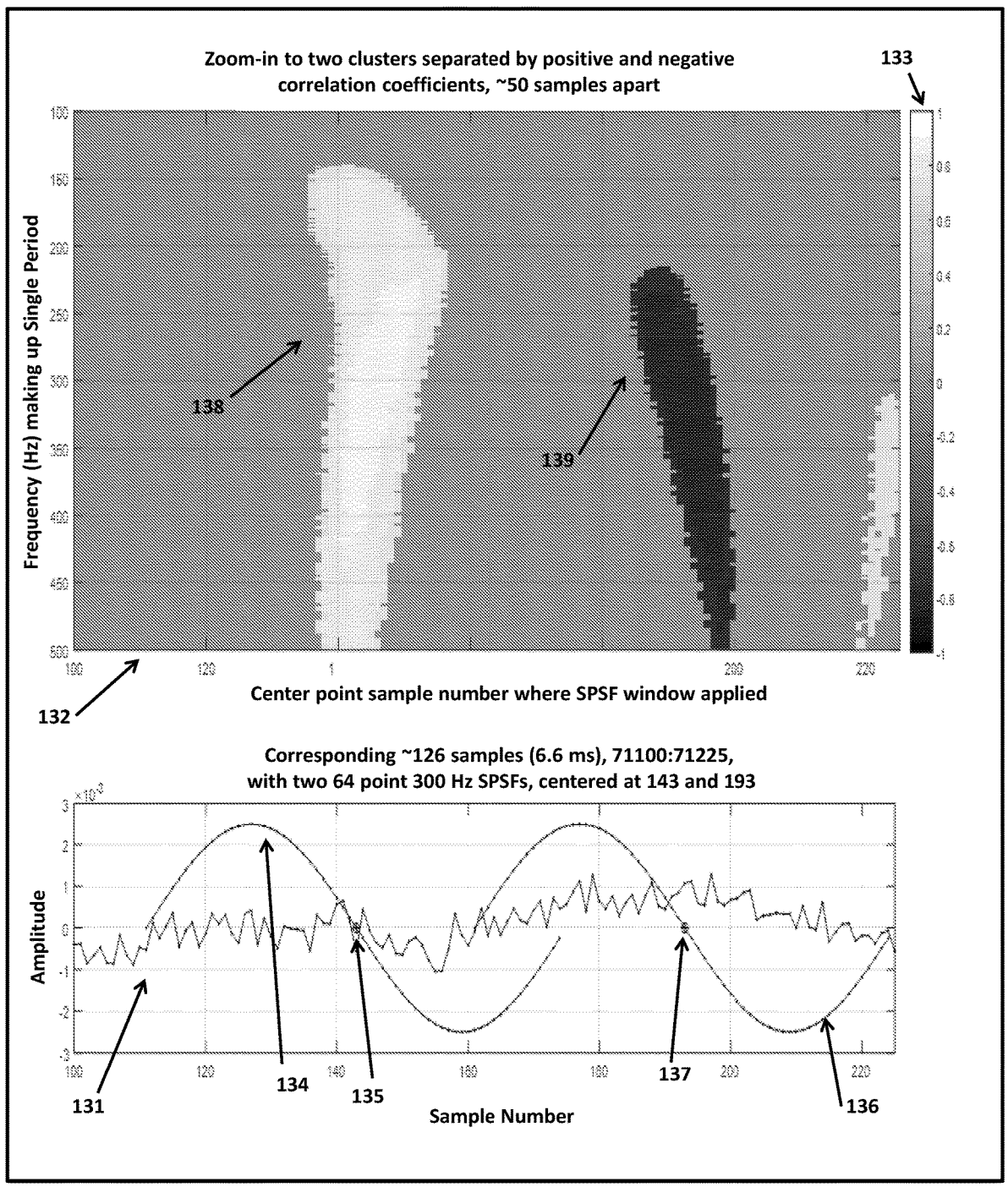
FIG. 13 has two plots that represent a zoom-in of FIG. 11, specifically sample points 100 to 220. The top plot (132) is a zoom-in of the FIG. 12 bottom plot (122). The highly positive CC patch (138) is a zoom-in of the FIG. 11 patch (126). A highly negative CC is indicated by pointer (139). Pointer (133) indicates the scale as described in FIG. 11. The bottom plot (131) zooms-in on the EEG samples corresponding to the samples shown in (132). There are two SPSFs (134, 136) overlaying the EEG along with their corresponding center points (135, 137) located at sample numbers 143 and 193.

FIG. 13 has two plots that represent a zoom-in of FIG. 12, specifically sample points 100 to 220. The top plot (132) is a zoom-in of the FIG. 12 bottom plot (122). The highly positive CC patch (138) is a zoom-in of the FIG. 12 patch (126). A highly negative CC is indicated by pointer (139). Pointer (133) indicates the scale as described in FIG. 11. The bottom plot (131) zooms-in on the EEG samples corresponding to the samples shown in (132). There are two SPSFs (134, 136) overlaying the EEG along with their corresponding center points (135, 137) located at sample numbers 143 and 193.

Together the top and bottom plots show that the SPSF detectors show highly positive correlation of an in-phase 300 Hz SPSF component, (134), starting at center sample number 143, which turns off after approximately 5 shifts of (134) to the right. As the (134) SPSF continues to move to the right, towards the SPSF at pointer (136), a highly negative correlation comes into view indicating the SPSF has shifted into an area of the EEG which contains a 180 degree out-of-phase section of a 300 Hz component. As the SPSF at (136) continues to move to the right, the method indicates the correlation is moving back between −0.75 and 0.75.

Figures 14, 14A, 14B:
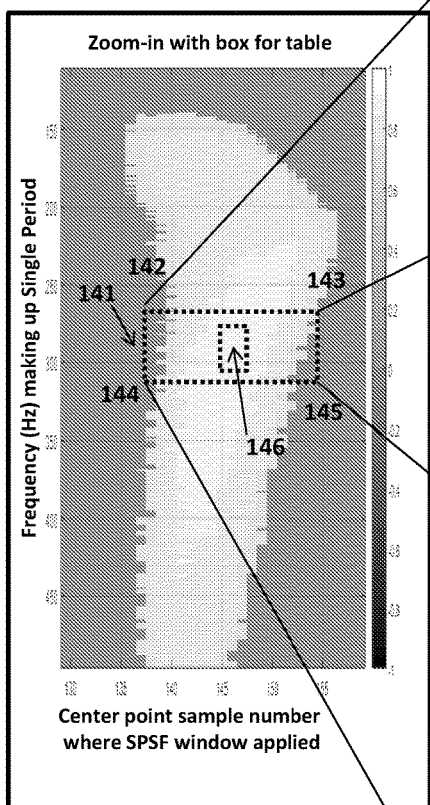
FIG. 14 focuses on the highly positive correlated patch (138) from FIG. 13 and how this patch would appear numerically in the CC matrix.
FIG. 14*a* is a zoom-in of the highly positive CC patch (138) of FIG. 13.
FIG. 14*b* shows a left column of numbers in bold listing the SPSF frequencies 260 to 290, a bottom row of numbers in bold representing the center sample numbers 138 to 155, and a matrix of CCs (multiplied by 100) inside a box of dashed line segments. The FIG. 14*a* pointer (131) indicates the box that encompasses the CCs shown in FIG. 14*b*. Pointers (142), (143), (144), and (145) are drawn to show how the corners of the box (141) and the matrix line-up with each other. Pointer (146) points to a smaller dashed box and it corresponds to the CC's found inside the smaller dashed box indicated in FIG. 14*b* by pointer (147).

FIG. 14 adds a numerical point of view to the matrix visualizations. FIG. 14 focuses on the highly positive correlated patch (138) from FIG. 13 and how this patch would appear numerically in the CC matrix. FIG. 14 is split into two parts 14a and 14b. FIG. 14a is a zoom-in of the highly positive CC patch (138) of FIG. 13. FIG. 14b shows a left column of numbers in bold listing the SPSF frequencies 260 to 290, a bottom row of numbers in bold representing the center sample numbers 138 to 155, and a matrix of CCs (multiplied by 100) inside a box of dashed line segments. The FIG. 14a pointer (131) indicates the box that encompasses the CCs shown in FIG. 14b. Pointers (142), (143), (144), and (145) are drawn to show how the corners of the box (141) and the matrix line-up with each other.

Pointer (146) points to a smaller dashed box and it corresponds to the CC's found inside the smaller dashed box indicated in FIG. 14b by pointer (147). The box indicated by 147 contains a correlation coefficient of 0.90 (but shown as 90 due the multiplication by 100). This correlation coefficient is the highest correlation anywhere in FIG. 14b. This indicates that the strongest presence of a 275 Hz SPSF element at the $146^{th}$ sample in time (EEG sample number 71246).

Figure 15:
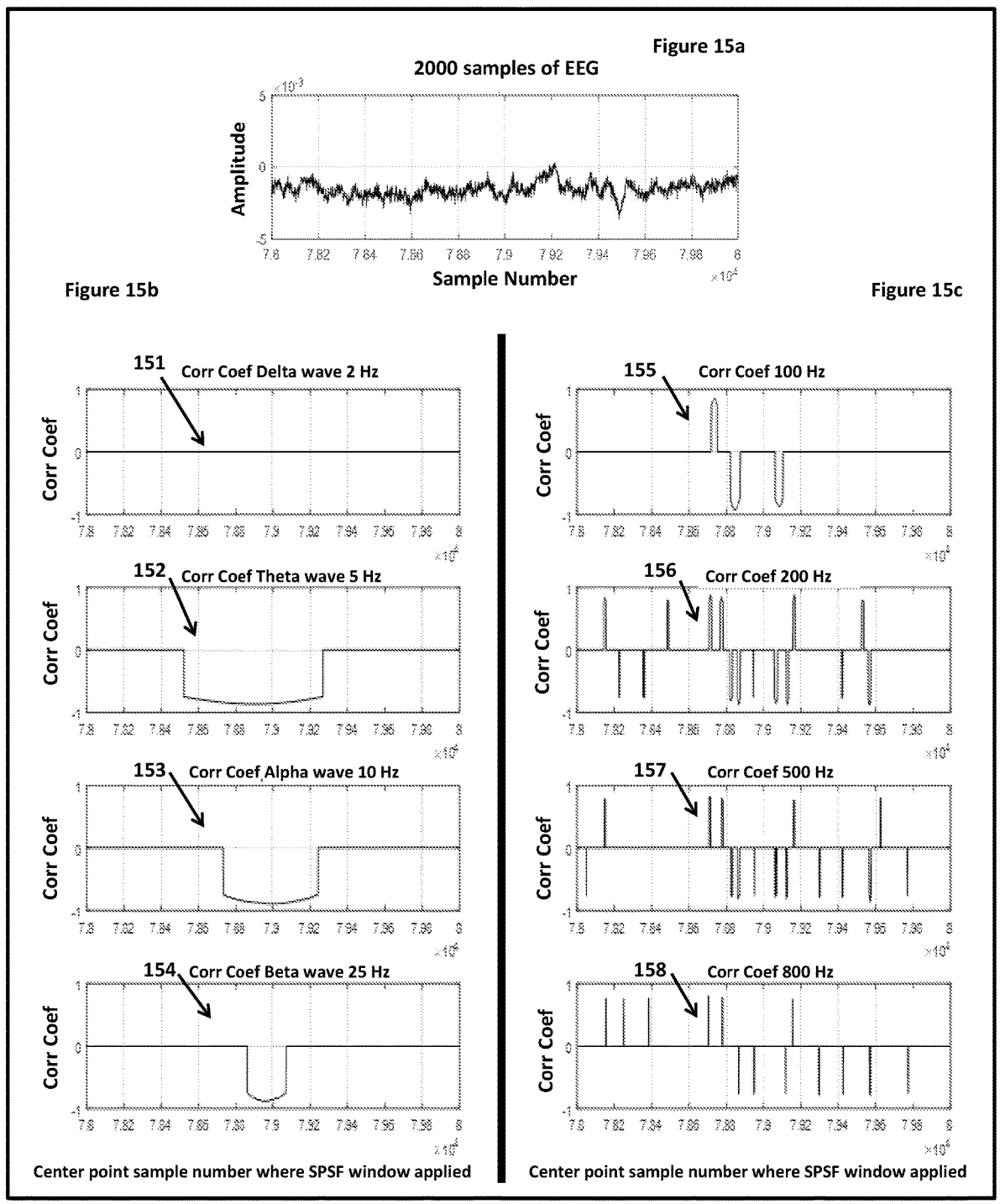
FIG. 15 is split into three parts.

FIG. 15 uses plots of individual rows of the SPSF matrix. The plots offer a better visual resolution with respect to meeting or exceeding the set threshold. Consistent with previous scales, all CCs between −0.75 and 0.75 have been set to zero; any non-zero point shown is either (>=0.75) or (<=−0.75).

FIG. 15 is split into three parts. FIG. 15a shows EEG sample points 78,001 to 80,000 (2,000 pts), taken from the last 2,000 points of FIG. 11 (111). FIG. 15b plots four individual rows of CCs taken from FIG. 11 (112), corresponding to the 2,000 center point sample numbers and four SBSF elements drawn from the commonly studied bands of (relatively) low frequencies: 2 Hz (Delta) wave, 5 Hz (Theta) wave, 10 Hz (Alpha) wave, and 25 Hz (Beta) wave. FIG. 15c plots four individual rows of CCs, corresponding to the 2,000 center point sample numbers and four SBSF elements from the less-commonly studied bands of (relatively high) frequencies, referred to as 'ripples': a 100 Hz wave, a 300 Hz wave, a 500 Hz wave, and a 800 Hz wave.

Pointers (151) through (158) indicate a neighborhood of samples, namely center point samples 78,600 to 79,000, to compare and contrast the CC responses among the eight selected frequencies.

A quality control check was put in place to test the robustness of the method. The electrode (11) in FIG. 1 was detached and was placed on a table. The remaining components were not changed. A 5 second recording was taken. The SPSF method was applied to the recording of the detached electrode in exactly the same way as it was applied to the EEG recording. An initial matrix was formed from the SPSF correlation coefficients with the full range of correlation coefficients ranging from −1.0 to 1.0; From said initial matrix a second matrix was formed by applying a threshold such that any entry of the matrix which is between the values of −0.75 and 0.75, (not inclusive), is set to zero, while the values that do not meet the threshold condition are not changed.

Figure 16:
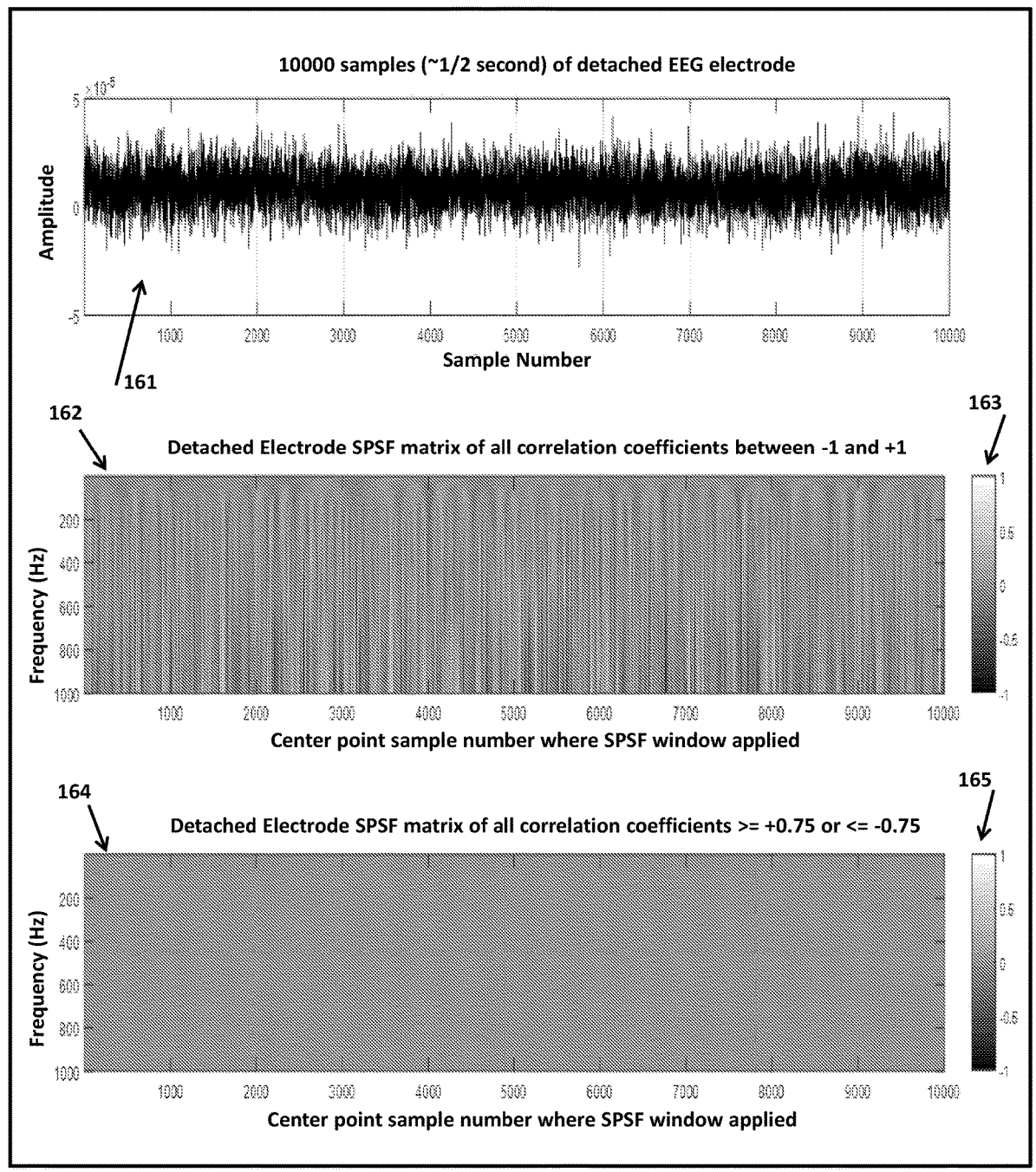
FIG. 16 has three plots. The top plot (161) is a collection of 10,000 samples recorded after detaching Electrode E14 from the skin and laying it on the table, with the electrode sensor facing up; hence this is not an EEG recording. The middle plot (162) shows the matrix of CCs for the 10,000 center point sample numbers and SPSF frequencies 1 to 1000. The scale (163) ranges from (−1 to 1) and the entries reflect any value from that range. The bottom plot (164) reflects the application of the same thresholds applied in FIGS. 7-12 such that entries which are (>=0.75) or (<=−0.75) follow the color bar scheme from the scale (165) for those values and any entry taking on a value between (−0.75 and 0.75) are set to the color associated with 0. The resulting matrix of (164) consists of all 0's.

FIG. 16 is the visualization of the results. FIG. 16 has three plots. The top plot (161) is a collection of 10,000 samples recorded after detaching Electrode E14 from the skin and laying it on the table, with the electrode sensor facing up; hence this is not an EEG recording. The middle plot (162) shows the matrix of CCs for the 10,000 center point sample numbers and SPSF frequencies 1 to 1000. The scale (163) ranges from (−1 to 1) and the entries reflect any value from that range. This is the type of thresholding configured in FIG. 7.

The bottom plot (164) reflects the application of the same thresholds applied in FIGS. 8-13 such that entries which are (>=0.75) or (<=−0.75) follow the color bar scheme from the scale (165) for those values and any entry taking on a value between (−0.75 and 0.75) are set to the color associated with 0. The resulting matrix of (164) was inspected and it was found that all entries had the value of zero and this is reflected in the matrix visualization

What is claimed is:

1. A computer implemented electroencephalogram (EEG) recording analysis method for implementing the filling of a matrix with correlation coefficient calculations as a function of an EEG sampling rate of an EEG recording, a plurality of time domain aligned portions of said EEG recording, and a plurality of single-period single-frequency (SPSF) sinusoids, the method comprising the steps of:
   (a) Configuring a computer to record into memory a bank of computer generated single-period sinusoids; wherein each said sinusoid is sampled at said EEG sampling rate; wherein said EEG sampling rate is defined by a predetermined number of data points recorded each second; wherein each said single-period sinusoid is based on an individual (single) frequency chosen from a set of frequencies that consists of integral multiples of 1 Hz not to exceed one-tenth of said EEG sampling rate; said bank of single-period single-frequency sinusoids herein referred to as a bank of SPSFs;

(b) Configuring said computer to retrieve from memory a starting section of contiguous samples of said EEG recording; wherein said starting section of contiguous samples comprises a sampled number of data points; wherein said sampled number is equal to said predetermined number of data points defining said EEG sampling rate;

(c) Storing into memory a center point sampling number from said starting section of contiguous samples, the center point sampling number being a data point associated with the EEG recording;

(d) Configuring said computer to retrieve an SPSF from said bank; align a center point of said SPSF to the center point sampling number of said starting section of contiguous samples; and configure a signal processing module to calculate a correlation coefficient between said aligned SPSF and said starting section of contiguous samples;

(e) Repeating step (d) for the remainder of said bank of SPSFs;

(f) Configuring said computer to record into memory said correlation coefficients calculated in steps (d) and (e) as entries of the first column of a matrix; wherein rows of said matrix are ordered such that row 1 corresponds to a 1 Hz SPSF and the last row corresponds to the SPSF with the highest integral frequency from said bank;

(g) Configuring said computer to retrieve a subsequent section of contiguous samples of said EEG recording from memory corresponding to a one sample shift to the right in time;

(h) Repeating steps (d) and (e) for the subsequent section of contiguous samples;

(i) Recording the subsequent correlation coefficients from (h) in the next column of said matrix; and (j) Repeating steps (g), (h), and (i).

2. A system facilitating the filling in of a matrix with correlation coefficient calculations implemented as a function of an EEG sampling rate of an EEG recording, a plurality of time domain aligned portions of said EEG recording, and a plurality of single-period single-frequency (SPSF) sinusoids, wherein the system comprises a processor configured to:

(a) Cause a computer system to record into memory a bank of computer generated single-period sinusoids; wherein each said sinusoid is sampled at said EEG sampling rate; wherein said EEG sampling rate is defined by a predetermined number of data points recorded each second; wherein each said single-period sinusoid is based on an individual (single) frequency chosen from a set of frequencies that consists of integral multiples of 1 Hz not to exceed one-tenth of said EEG sampling rate; said bank of single-period single-frequency sinusoids herein referred to as a bank of SPSFs;

(b) Cause said computer system to retrieve from memory a starting section of contiguous samples of said EEG recording; wherein said starting section of contiguous samples comprises a sampled number of data points; wherein said sampled number is equal to said predetermined number of data points defining said EEG sampling rate;

(c) Store into memory a center point sampling number from said starting section of contiguous samples, the center point sampling number being a data point associated with the EEG recording;

(d) Cause said computer system to retrieve an SPSF from said bank; align a center point of said SPSF to the center point sampling number of said starting section of contiguous samples; configure a signal processing module to calculate a correlation coefficient between said aligned SPSF and said starting section of contiguous samples;

(e) Repeat step (d) for the remainder of SPSFs from said bank;

(f) Cause said computer system to record into memory said correlation coefficients calculated in steps (d) and (e) as entries of the first column of a matrix; wherein rows of said matrix are ordered such that row 1 corresponds to a 1 Hz SPSF and the last row corresponds to the SPSF with the highest integral frequency from said bank;

(g) Cause said computer system to retrieve a subsequent section of contiguous samples of said EEG recording from memory corresponding to a one sample shift to the right in time;

(h) Cause said computer system to repeat steps (d) and (e) for the subsequent section of contiguous samples;

(i) Cause said computer system to record the subsequent correlation coefficients from (h) in the next column of said matrix; and (j) Cause said computer system to repeat steps (g), (h), and (i).

3. A computer program product for calculating a correlation coefficient as a function of an EEG sampling rate of an EEG recording, a plurality of time domain aligned portions of said EEG recording, and a plurality of single-period single-frequency (SPSF) sinusoids, said computer program product comprising a non-transitory computer readable storage medium, the non-transitory computer readable storage medium comprising computer executable instructions, which when executed, cause a processor to:

(a) Record into memory a bank of computer generated single-period sinusoids; wherein each said sinusoid is sampled at said EEG sampling rate; wherein said EEG sampling rate is defined by a predetermined number of data points recorded each second; wherein each said single-period sinusoid is based on an individual (single) frequency chosen from a set of frequencies that consists of integral multiples of 1 Hz not to exceed one-tenth of said EEG sampling rate; said bank of single-period single-frequency sinusoids herein to be referred to as a bank of SPSFs;

(b) Retrieve from memory a starting section of contiguous samples of said EEG recording; wherein said starting section of contiguous samples comprises a sampled number of data points; wherein said sampled number is equal to said predetermined number of data points defining said EEG sampling rate;

(c) Store into memory a center point sampling number from said starting section of contiguous samples, the center point sampling number being a data point associated with the EEG recording;

(d) Retrieve an SPSF from said bank of SPSFs; align a center point of said SPSF to the center point sampling number of said starting section of contiguous samples; configure a signal processing module to calculate a correlation coefficient between said aligned SPSF and said starting section of contiguous samples;

(e) Repeat step (d) for the remainder of SPSFs from said bank;
(f) Record into memory said correlation coefficients calculated in steps (d) and (e) as entries of the first column of a matrix; wherein rows of said matrix are ordered such that row 1 corresponds to a 1 Hz SPSF and the last row corresponds to the SPSF with the highest integral frequency from said bank;
(g) Retrieve a subsequent section of contiguous samples of said EEG recording from memory corresponding to a one sample shift to the right in time;
(h) Repeat steps (d) and (e) for the subsequent section of contiguous samples;
(i) Record the subsequent correlation coefficients from (h) in the next column of said matrix; and
(j) Repeat steps (g), (h), and (i).

* * * * *